US009168292B2

(12) United States Patent
Rodriguez-Munoz et al.

(10) Patent No.: US 9,168,292 B2
(45) Date of Patent: Oct. 27, 2015

(54) HETEROLOGOUS PRIME BOOST VACCINATION REGIMEN AGAINST MALARIA

(75) Inventors: Ariane Rodriguez-Munoz, Leiden (NL); Katarina Radosevic, Nootdorp (NL); Angelique Alida Corina Lemckert, Voorschoten (NL)

(73) Assignee: Crucell Holland B.V., Leiden (NL)

( * ) Notice: Subject to any disclaimer, the term of this patent is extended or adjusted under 35 U.S.C. 154(b) by 4 days.

(21) Appl. No.: 13/823,581

(22) PCT Filed: Sep. 7, 2011

(86) PCT No.: PCT/EP2011/065434
§ 371 (c)(1),
(2), (4) Date: Mar. 14, 2013

(87) PCT Pub. No.: WO2012/041669
PCT Pub. Date: Apr. 5, 2012

(65) Prior Publication Data
US 2013/0216580 A1 Aug. 22, 2013

Related U.S. Application Data

(60) Provisional application No. 61/404,156, filed on Sep. 27, 2010.

(30) Foreign Application Priority Data

Sep. 27, 2010 (EP) .................................... 10180251

(51) Int. Cl.
*F16K 31/62* (2006.01)
*A61K 39/015* (2006.01)
*C12N 15/86* (2006.01)
*A61K 39/00* (2006.01)

(52) U.S. Cl.
CPC .............. *A61K 39/015* (2013.01); *C12N 15/86* (2013.01); *A61K 2039/5256* (2013.01); *A61K 2039/545* (2013.01); *A61K 2039/55555* (2013.01); *A61K 2039/55566* (2013.01); *A61K 2039/55577* (2013.01); *C12N 2710/10343* (2013.01); *C12N 2710/10362* (2013.01); *C12N 2710/10371* (2013.01); *C12N 2799/022* (2013.01)

(58) Field of Classification Search
None
See application file for complete search history.

(56) References Cited

U.S. PATENT DOCUMENTS

| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,981,225 A | 11/1999 | Kochanek et al. |
| 5,994,128 A | 11/1999 | Fallaux et al. |
| 6,005,009 A | 12/1999 | Murad et al. |
| 6,020,191 A | 2/2000 | Scaria et al. |
| 6,040,174 A | 3/2000 | Imler et al. |
| 6,113,913 A | 9/2000 | Brough et al. |
| 6,225,289 B1 | 5/2001 | Kovesdi et al. |
| 6,261,823 B1 | 7/2001 | Tang et al. |
| 2005/0208078 A1* | 9/2005 | Hoffman et al. ............ 424/272.1 |
| 2005/0265974 A1* | 12/2005 | Pau et al. ...................... 424/93.2 |
| 2005/0266017 A1* | 12/2005 | Druilhe et al. ............. 424/191.1 |
| 2006/0188527 A1* | 8/2006 | Hoffman et al. ............ 424/272.1 |
| 2009/0110695 A1* | 4/2009 | Havenga et al. ............ 424/199.1 |
| 2012/0082694 A1* | 4/2012 | Pau et al. ................... 424/191.1 |

FOREIGN PATENT DOCUMENTS

| EP | 0468520 | 7/1991 |
| EP | 0549074 B1 | 12/1992 |
| EP | 0689454 | 3/1994 |
| EP | 0729473 B1 | 11/1994 |
| EP | 0853660 | 7/1997 |

(Continued)

OTHER PUBLICATIONS

Charoenvit et al (Science vol. 251, pp. 668-671, 1991.*
International Search Report PCT/EP2011/065434, dated Sep. 7, 2011.
Written Opinion of the International Searching Authority, PCT/EP2011/065434, dated Sep. 7, 2011.
RadosEvic' et al., The Th1 Immune Response to *Plasmodium falciparum* Circumsporozoite Protein Is Boosted by Adenovirus Vectors 35 and 26 with a Homologous Insert, Clinical and Vaccine Immunology, dated Nov. 2010, pp. 1687-1694, vol. 17, No. 11.

(Continued)

*Primary Examiner* — Gary Nickol
*Assistant Examiner* — Khatol Shahnan Shah
(74) *Attorney, Agent, or Firm* — TraskBritt, P.C.

(57) ABSTRACT

Described are methods for inducing an immune response in a subject against an antigen from a malaria-causing parasite, preferably *P. falciparum*, the method comprising: (i) administering to a subject a priming composition comprising adjuvanted proteinaceous antigen-comprising circumsporozoite (CS) protein or an immunogenic part thereof from a malaria-causing parasite; (ii) administering to the subject a first boosting composition comprising a recombinant adenovirus vector that comprises nucleic acid encoding CS protein or immunogenic part thereof from a malaria-causing parasite; and (iii) administering to the subject a second boosting composition comprising a recombinant adenovirus vector that comprises nucleic acid encoding CS protein or an immunogenic part thereof from a malaria-causing parasite, wherein either the first boosting composition comprises a recombinant adenovirus vector of serotype 35 (Ad35) and the second boosting composition comprises a recombinant adenovirus of Ad26, or wherein the first boosting composition comprises a recombinant adenovirus vector of Ad26 and the second boosting composition comprises a recombinant adenovirus of Ad35.

20 Claims, 7 Drawing Sheets

(56) References Cited

FOREIGN PATENT DOCUMENTS

| | | |
|---|---|---|
| EP | 0362279 B1 | 1/1998 |
| WO | WO 93/10152 | 5/1993 |
| WO | WO 94/00153 | 1/1994 |
| WO | WO 95/17210 | 6/1995 |
| WO | WO 96/02555 | 2/1996 |
| WO | WO 96/11711 | 4/1996 |
| WO | WO 96/33739 | 10/1996 |
| WO | WO 98/05355 | 2/1998 |
| WO | WO 98/15287 | 4/1998 |
| WO | WO 98/22588 | 5/1998 |
| WO | WO 98/56414 | 12/1998 |
| WO | WO 99/10008 | 3/1999 |
| WO | WO 99/11241 | 3/1999 |
| WO | WO 99/12565 | 3/1999 |
| WO | WO 99/12568 | 3/1999 |
| WO | WO 99/41416 | 8/1999 |
| WO | WO 00/29024 | 5/2000 |
| WO | WO 00/32754 | 6/2000 |
| WO | WO 00/70071 | 11/2000 |
| WO | WO 01/66137 | 9/2001 |
| WO | WO 03/049763 | 6/2003 |
| WO | WO 03/061708 | 7/2003 |
| WO | WO 03/078592 | 9/2003 |
| WO | WO 03/104467 | 12/2003 |
| WO | WO 04/001032 | 12/2003 |
| WO | WO 2004/020971 | 3/2004 |
| WO | WO 2004/055187 | 7/2004 |
| WO | WO 2005/080556 | 9/2005 |
| WO | WO 2006/040334 | 4/2006 |
| WO | WO 2006/108707 | 10/2006 |
| WO | WO 2007/110409 | 10/2007 |
| WO | WO 2009/117134 | 9/2009 |
| WO | WO 2010/060719 | 6/2010 |
| WO | WO 2011/098592 A1 | 8/2011 |

OTHER PUBLICATIONS

Rodríguez et al., Evaluation of a prime-boost vaccine schedule with distinct adenovirus vectors against malaria in rhesus monkeys, Vaccine, www.elsevier.com/locate/vaccine, dated 2009, pp. 6226-6233.

Stewart et al., Priming with an Adenovirus 35-Circumsporozoite Protein (CS) Vaccine followed by RTS,S/AS01B Boosting Significantly Improves Immunogenicity to *Plasmodium falciparum* CS Compared to That with Either Malaria Vaccine Alone, Infection and Immunity, May 2007, pp. 2283-2290, vol. 75, No. 5.

\* cited by examiner

HETEROLOGOUS PRIME BOOST VACCINATION REGIMEN AGAINST MALARIA

CROSS-REFERENCE TO RELATED APPLICATIONS

This application is a national phase entry under 35 U.S.C. §371 to PCT International Application No. PCT/EP2011/065434, filed on Sep. 7, 2011, designating the United States of America, and published in English as WO 2012/041669 A1 on Apr. 5, 2012, which itself claims priority under Article 8 of the PCT from EP 10180251.0, filed Sep. 27, 2010, and claims benefit under Article 8 of the PCT and 35 U.S.C. §119(e) of U.S. Ser. No. 61/404,156, filed on Sep. 27, 2010.

TECHNICAL FIELD

The disclosure relates to the field of health care. More particularly, it concerns novel regimens for vaccination against malaria.

BACKGROUND

Malaria currently represents one of the most prevalent infections in tropical and subtropical areas throughout the world. Per year, malaria infections kill up to 2.7 million people in developing and emerging countries. The widespread occurrence and elevated incidence of malaria are a consequence of the increasing numbers of drug-resistant parasites and insecticide-resistant parasite vectors. Other factors include environmental and climatic changes, civil disturbances and increased mobility of populations.

Malaria is caused by mosquito-borne hematoprotozoan parasites belonging to the genus *Plasmodium*. Four species of *Plasmodium* protozoa (*P. falciparum, P. vivax, P. ovale* and *P. malariae*) are responsible for the disease in man; many others cause disease in animals, such as *P. yoelii, P. knowlesi* and *P. berghei*. *P. falciparum* accounts for the majority of infections in humans and is the most lethal type.

The two major arms of the pathogen-specific immune response that occur upon entry of the parasite into the body are cellular and humoral. The one arm, the cellular response, relates to CD8+ and CD4+ T cells that participate in the immune response. Cytotoxic T lymphocytes (CTLs) express CD8 and are able to specifically kill infected cells that express pathogenic antigens on their surface. CD4+ T cells or T helper cells support the development of CTLs, produce various cytokines, and also help induce B cells to divide and produce antibodies specific for the antigens. During the humoral response, B cells specific for a particular antigen become activated, replicate, differentiate and produce antigen-specific antibodies.

Both arms of the immune response are relevant for protection against a malarial infection. A possible malaria vaccine approach would be most beneficial if it would induce a strong cellular immune response as well as a strong humoral immune response. It is widely accepted that persistent protective immunity against malaria likely requires high levels of Th1 type immune responses targeting the pre-erythrocytic stage of the malaria parasites.

However, almost forty years after the feasibility of vaccination against malaria was first demonstrated by means of irradiated sporozoites, a vaccine modality that efficiently induces long-lived protective immunity remains elusive. The most advanced CS-based malaria vaccine candidate to date is RTS,S, a vaccine based on a fragment of *Plasmodium falciparum* circumsporozoite (CS) protein, fused to and admixed with hepatitis B surface protein. This vaccine confers short-term protection against malaria infection with an efficacy of about 50% and induces particularly B-cell and CD4+ T-cell responses.

Albeit our understanding about the correlate(s) of protection for malaria is limited, there is ample evidence that circumsporozoite (CS) protein-specific antibodies, CD8+ T cells and Th1 cytokines, and, in particular, IFNγ, play a central role in controlling the pre-erythrocytic and early liver stages of malaria. Adenoviral vectors appear particularly suited for induction of IFNγ-producing $CD8^+$ T cells required to combat malaria infection (Ophorst et al., 2006; Rodrigues et al., 1997), due to intracellular expression of a transgene inserted in the vector genome and efficient routing of expressed protein toward the class I presentation pathway.

WO 2006/040334 describes prime boost regimens for malaria vaccination by administering a replication-defective recombinant adenovirus comprising nucleic acid encoding a CS antigen from a malaria-causing parasite and further administering adjuvanted proteinaceous antigen comprising a CS protein or immunogenic fragment thereof, and, amongst many other possibilities, describes adenovirus serotype 35 (Ad35) and Ad26 as preferred adenoviruses. WO 2006/040334 teaches that priming with the viral vector and boosting with the proteinaceous antigen provides superior results in terms of immune responses compared to the reverse regimen, in particular, with respect to IFN-γ T-cell responses. A particularly preferred regimen described therein comprises priming with Ad35 encoding a *P. falciparum* CS antigen and boosting twice with RTS,S. Indeed, this regimen is also demonstrated to be superior to the regimen wherein the order of administration of the protein and adenovirus are reversed in the article by Stewart et al., 2007. Thus, Ad35 with a CS antigen appears to be a very suitable priming vaccine for boosting by CS protein.

Antibody as well as robust IFN-γ responses against the CS antigen have also been reported upon a heterologous prime boost vaccination schedule wherein Ad35 encoding CS was boosted with Ad5 encoding CS (Rodriguez et al., 2009).

It has also been shown for the LSA-1 antigen that Ad35 priming followed by protein boosting results in induction of IFN-γ producing CD4+ and CD8+ T cells, although it could also be seen that the types of immune responses might differ between different transgenes, e.g., CS antigen may behave different from, e.g., LSA-1 antigen (Rodriguez et al., 2008).

In the experience of the inventors, several other prime boost regimens may be different regarding the level of immune responses depending on the antigen, and/or directionality of the prime-boost with respect to the vector used (see also, e.g., Abbink et al., 2007).

Unpredictability of immune responses with respect to different antigens is further underscored by the observation that recombinant BCG (rBCG) expressing *P. falciparum* CS protein neither resulted in detectable CS responses when administered alone, nor primed CS responses in a prime-boost schedule with Ad35 expressing CS (unpublished), whereas, in contrast, another antigen cloned in rBCG could be boosted by subsequent administration of an adenoviral vector with the same transgene and the same has been shown for vaccination against tuberculosis (TB) by BCG followed by heterologous booster constructs containing TB transgenes (see Cayabyab et al., 2009, and references therein).

Thus, the level and type of immune responses upon vaccination is complex and not fully predictable because it may differ for different transgenes and depend on the type of antigen and administration regimen.

In addition, the most preferred regimen known to date requires Ad35 with a CS antigen followed by two boosts with RTS,S (WO 2006/040334; Stewart et al., 2007). Production of RTS,S (adjuvanted protein) is much more expensive than production of adenoviral vectors, and addition of adjuvant is by definition related to a possibility of more (local) side effects, as is known to the skilled person. Thus, administration regimens requiring less adjuvanted protein such as RTS,S while still being capable of strong immune responses would be beneficial.

DISCLOSURE

Thus, there remains a need in the art for further effective vaccines and regimens for inducing strong immune responses against malaria antigens, preferably of both arms of the immune system and comprising a strong Th1 response. In addition, it would be beneficial if such regimens would require less administrations of adjuvanted protein. The instant disclosure aims at providing such regimens.

Demonstrated is that a Th1 immune response to CS protein, in particular, the CD8+ T-cell response, which is needed for strong and lasting malaria immunity, is boosted to sustainable levels using the Ad35.CS/Ad26.CS combination, while at the same time, a high level of antibody response is maintained. In this study, we evaluated immune responses induced with vaccination regimens based on an adjuvanted yeast-produced complete CS protein followed by two recombinant low seroprevalent adenoviruses expressing *P. falciparum* CS antigen, Ad35.CS (subgroup B) and Ad26.CS (subgroup D). Our results show that (i) the yeast-produced adjuvanted full-length CS protein is highly potent in inducing high CS-specific humoral responses in mice, but poor T-cell response; (ii) the Ad35.CS vector boosts the IFNγ+ CD8+ T-cell response induced by the CS protein immunization and shifts the immune response toward the Th1 type; and (iii) a three-component heterologous vaccination comprised of a CS protein prime, followed by boosts with Ad35.CS and Ad26.CS, elicits an even more robust and sustainable IFNγ+ CD8+ T-cell response as compared to one or two component regimens. The Ad35.CS/Ad26.CS combination boosted particularly the IFNγ+ and TNFα+ T cells, confining the shift of the immune response from the Th2 to Th1 type. The levels of cellular immunity reported herein may warrant a high level of protection against malaria based on long-term polyfunctional T-cell responses.

These results support the notion of first immunizations of infants with an adjuvanted CS protein vaccine, followed by a booster Ad35.CS/Ad26.CS vaccine at a later age to induce lasting protection against malaria for which the Th1 response and immune memory is required.

Thus, provided is a method for inducing an immune response in a subject against an antigen from a malaria-causing parasite, the method comprising: (i) administering to a subject a priming composition comprising adjuvanted proteinaceous antigen comprising circumsporozoite (CS) protein or immunogenic part thereof from a malaria-causing parasite; (ii) administering to the subject a first boosting composition comprising a recombinant adenovirus vector that comprises nucleic acid encoding CS protein or immunogenic part thereof from a malaria-causing parasite; and (iii) administering to the subject a second boosting composition comprising a recombinant adenovirus vector that comprises nucleic acid encoding CS protein or immunogenic part thereof from a malaria-causing parasite.

Also provided is a method for inducing an immune response in a subject against an antigen from a malaria-causing parasite, the method comprising: administering to a subject to which a priming composition comprising adjuvanted proteinaceous antigen comprising CS protein or immunogenic part thereof from a malaria-causing parasite has been administered: (a) a first boosting composition comprising a recombinant adenovirus vector that comprises nucleic acid encoding CS protein or immunogenic part thereof from a malaria-causing parasite; and (b) a second boosting composition comprising a recombinant adenovirus vector that comprises nucleic acid encoding CS protein or immunogenic part thereof from a malaria-causing parasite.

Further provided is a method for inducing an immune response in a subject against an antigen from a malaria-causing parasite, the method comprising: administering to a subject to which a priming composition comprising adjuvanted proteinaceous antigen comprising CS protein or immunogenic part thereof from a malaria-causing parasite, and a first boosting composition comprising a recombinant adenovirus vector that comprises nucleic acid encoding CS protein or immunogenic part thereof from a malaria-causing parasite have been administered; a second boosting composition comprising a recombinant adenovirus vector that comprises nucleic acid encoding CS protein or immunogenic part thereof from a malaria-causing parasite.

Further provided is (i) a priming composition comprising adjuvanted proteinaceous antigen comprising CS protein or immunogenic part thereof from a malaria-causing parasite; (ii) a first boosting composition comprising a recombinant adenovirus vector that comprises nucleic acid encoding CS protein or immunogenic part thereof from a malaria-causing parasite; and (iii) a second boosting composition comprising a recombinant adenovirus vector that comprises nucleic acid encoding CS protein or immunogenic part thereof from a malaria-causing parasite, for use in inducing an immune response in a subject against an antigen from a malaria-causing parasite by administering to the subject the priming composition, the first boosting composition and the second boosting composition in that order.

Provided is a first boosting composition comprising a recombinant adenovirus vector that comprises nucleic acid encoding CS protein or immunogenic part thereof from a malaria-causing parasite and a second boosting composition comprising a recombinant adenovirus vector that comprises nucleic acid encoding CS protein or immunogenic part thereof from a malaria-causing parasite, for use in inducing an immune response in a subject against an antigen from a malaria-causing parasite by administering to the subject the first boosting composition and the second boosting composition in that order, wherein a priming composition comprising adjuvanted proteinaceous antigen comprising CS protein or immunogenic part thereof from a malaria-causing parasite has previously been administered to the subject.

Provided is a second boosting composition comprising a recombinant adenovirus vector that comprises nucleic acid encoding CS protein or immunogenic part thereof from a malaria-causing parasite for use in inducing an immune response in a subject against an antigen from a malaria-causing parasite by administering to the subject the second boosting composition, wherein a priming composition comprising adjuvanted proteinaceous antigen comprising CS protein or immunogenic part thereof from a malaria-causing parasite and a first boosting composition comprising a recombinant adenovirus vector that comprises nucleic acid encoding CS protein or immunogenic part thereof from a malaria-causing parasite have previously been administered to the subject in that order.

Provided is the use of (i) a priming composition comprising adjuvanted proteinaceous antigen comprising CS protein or immunogenic part thereof from a malaria-causing parasite; (ii) a first boosting composition comprising a recombinant adenovirus vector that comprises nucleic acid encoding CS protein or immunogenic part thereof from a malaria-causing parasite; and (iii) a second boosting composition comprising a recombinant adenovirus vector that comprises nucleic acid encoding CS protein or immunogenic part thereof from a malaria-causing parasite, for the preparation of a medicament for inducing an immune response in a subject against an antigen from a malaria-causing parasite by administering to the subject the priming composition, the first boosting composition and the second boosting composition in that order.

Further provided is the use of a first boosting composition comprising a recombinant adenovirus vector that comprises nucleic acid encoding CS protein or immunogenic part thereof from a malaria-causing parasite and a second boosting composition comprising a recombinant adenovirus vector that comprises nucleic acid encoding CS protein or immunogenic part thereof from a malaria-causing parasite, for the manufacture of a medicament for inducing an immune response in a subject against an antigen from a malaria-causing parasite by administering to the subject the first boosting composition and the second boosting composition in that order, wherein a priming composition comprising adjuvanted proteinaceous antigen comprising CS protein or immunogenic part thereof from a malaria-causing parasite has previously been administered to the subject.

Further provided is the use of a second boosting composition comprising a recombinant adenovirus vector that comprises nucleic acid encoding CS protein or immunogenic part thereof from a malaria-causing parasite for the manufacture of a medicament for inducing an immune response in a subject against an antigen from a malaria-causing parasite by administering to the subject the second boosting composition, wherein a priming composition comprising adjuvanted proteinaceous antigen comprising CS protein or immunogenic part thereof from a malaria-causing parasite and a first boosting composition comprising a recombinant adenovirus vector that comprises nucleic acid encoding CS protein or immunogenic part thereof from a malaria-causing parasite have previously been administered to the subject in that order.

In the foregoing, either the first boosting composition comprises a recombinant adenovirus vector of serotype 35 (Ad35) and the second boosting composition comprises a recombinant adenovirus of Ad26, or, alternatively, the first boosting composition comprises a recombinant adenovirus vector of Ad26 and the second boosting composition comprises a recombinant adenovirus of Ad35.

hereof

In certain embodiments, the first boosting composition comprises a recombinant adenovirus vector of Ad35 and the second boosting composition comprises a recombinant adenovirus of Ad26.

In preferred embodiments, the malaria-causing parasite is *Plasmodium falciparum*.

In certain embodiments, the adjuvanted proteinaceous antigen comprising CS protein or immunogenic part thereof from a malaria-causing parasite in the priming composition comprises RTS,S.

In preferred embodiments, the immune response comprises a CS-specific CD8+ T-cell response.

In preferred embodiments, the immune response comprises inducing CS-specific IFNγ+ CD8+ and TNFα+CD8+ T-cells.

In preferred embodiments, the immune response comprises a Th1 type T-cell response.

In preferred embodiments, inducing the immune response comprises shifting the CS-specific immune response (from a Th2 type) toward a balanced Th1 and Th2 type or a more dominant Th1 type of response.

In preferred embodiments, the immune response comprises a CS-specific B-cell response.

In certain embodiments, the priming composition is administered or has been administered to the subject where the subject had or has an age of about six weeks, and the first boosting composition is administered or has been administered to the subject about four weeks after administration of the priming composition and the second boosting composition is administered to the subject about four weeks after administration of the first priming composition.

DETAILED DESCRIPTION

Figure 1:
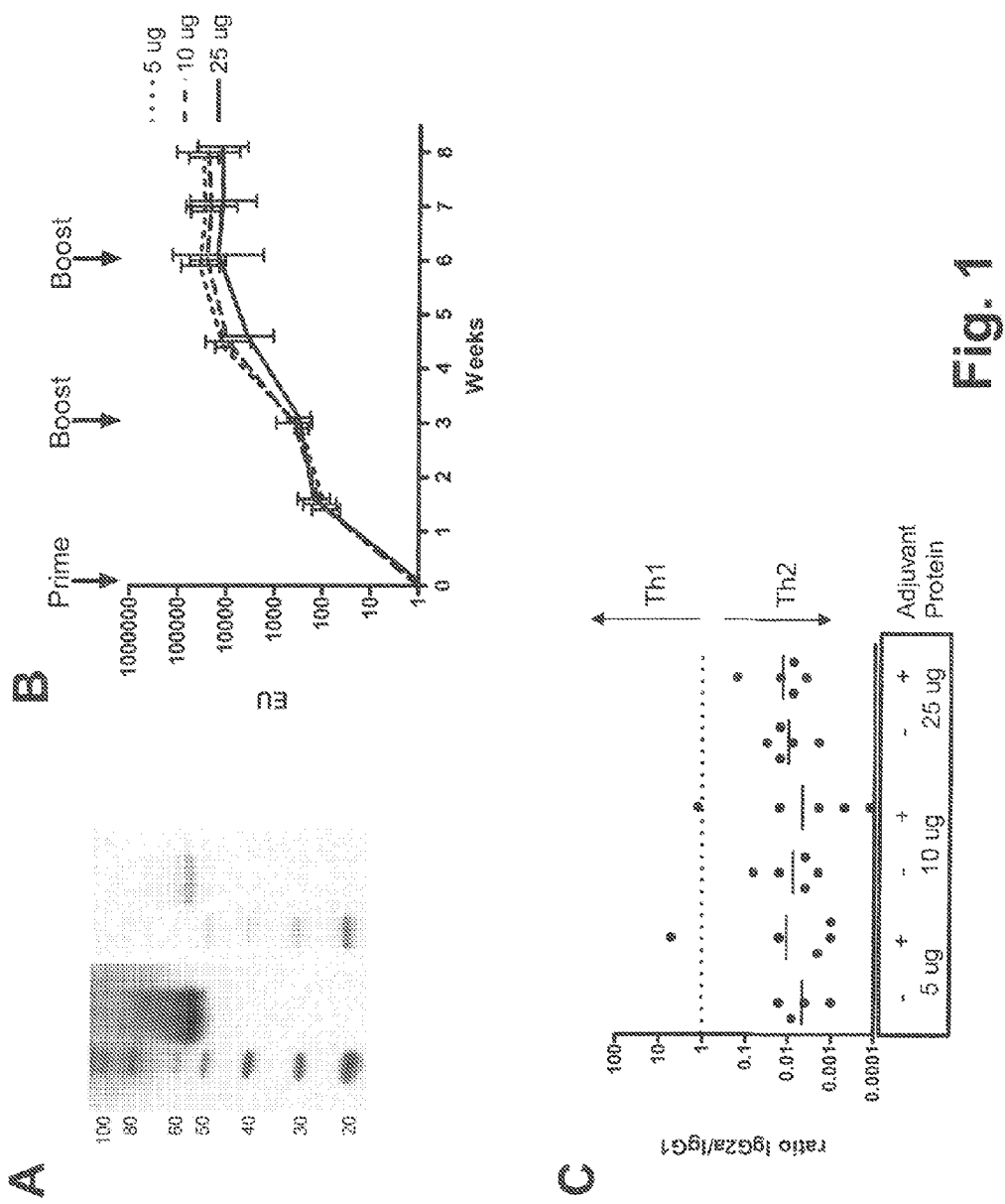
FIG. 1. Characterization of the yeast-produced CS protein. (A) The yeast-produced CS protein was analyzed by CS-specific Western blot and InstantBlue staining. (B) BALB/c mice (n=five per group) were immunized s.c. three times with 5, 10 or 25 µg montanide ISA720 adjuvanted CS protein at three-week intervals. CS-specific humoral responses were assessed every 1.5 weeks up to eight weeks after the initial immunization by ELISA. Mean titers with 95% confidence interval are depicted. EU; ELISA units. (C) IgG2a/IgG1 ratios upon measurement of CS-specific IgG2a and IgG1 responses eight weeks after the initial immunization. Bars represent geometric means IgG2a/IgG 1 ratios.

A malaria-causing parasite hereof is from the genus *Plasmodium*, and can, for instance, be *Plasmodium* (P.) *falciparum*, *P. vivax*, *P. ovale*, *P. malariae*, *P. yoelii*, *P. knowlesi* or *P. berghei*. The preferred malaria-causing parasite hereof is *P. falciparum*.

A subject hereof preferably is a mammal that is capable of being infected with a malaria-causing parasite, for instance, a mouse, a non-human-primate or a human. Preferably, the subject is a human subject.

A proteinaceous antigen comprises a polypeptide, which may optionally further comprise modifications and/or additions, such as lipids. In certain embodiments, a proteinaceous antigen is a protein, a glycosylated protein, or a lipoprotein.

A preferred proteinaceous antigen comprising CS protein or immunogenic part thereof from a malaria-causing parasite comprises a hybrid protein of CS protein or an immunogenic fragment thereof fused to the surface antigen from hepatitis B virus (HbsAg), in the form of lipoprotein particles with HbsAg. In a preferred embodiment, the proteinaceous antigen comprises RTS,S.

Provided are methods comprising administering to a subject a priming composition comprising adjuvanted proteinaceous antigen comprising CS protein or immunogenic part thereof, which is also referred to herein as the priming vaccine or priming vaccination; subsequent steps of the methods comprise administering to the subject a first boosting composition comprising a recombinant adenovirus vector that comprises nucleic acid encoding CS protein or immunogenic part thereof, and again subsequently administering to the subject a second boosting composition comprising a recombinant adenovirus vector that comprises nucleic acid encoding CS protein or immunogenic part thereof, which are also referred to herein as the first and second booster/boosting vaccine/vaccination, respectively, or booster/boosting vaccines/vaccination collectively.

The adjuvanted proteinaceous antigen for use in any or all aspects hereof may comprise the CS protein from *P. falciparum*, or an immunogenic fragment thereof. In certain embodiments, it comprises a full-length CS protein, and in other embodiments, it comprises an immunogenic part of the CS protein. Immunogenic parts of the CS protein are known to the skilled person. In certain embodiments, the proteinaceous antigen comprises the CS protein or immunogenic part thereof in the form of a fusion protein. A proteinaceous antigen can be produced according to routine methods well known to the skilled person, e.g., by recombinant expression in one of many available expression systems, e.g., bacteria such as *E. coli*, but preferably in eukaryotic expression systems such as, for example, yeast, insect cells or mammalian cell lines such as Chinese Hamster Ovary cells or human cell lines. For example, the antigen may comprise a hybrid protein of CS protein or an immunogenic fragment fused to the surface antigen from hepatitis B virus (HBsAg), which hybrid protein may be expressed in prokaryotic or eukaryotic host cells and may take the form of lipoprotein particles. The fusion protein may comprise, for example, substantially all the C-terminal portion of the CS protein, four or more tandem repeats of the immunodominant region, and the surface antigen from hepatitis B virus (HBsAg). For example, the hybrid protein comprises a sequence that contains at least 160 amino acids, which is substantially homologous to the C-terminal portion of the CS protein and may be devoid of the end amino acids from the C-terminal of the CS protein, for example, the last 10 to 12 amino acids. The hybrid protein may be in the form of mixed lipoprotein particles, for example, with HBsAg.

In particular, there is provided a hybrid protein as disclosed in WO 93/10152, designated therein as "RTS*" but referred to herein as "RTS," which may be in the form of mixed lipoprotein particles with HBsAg, herein designated RTS,S. The ratio of hybrid protein:S antigen in these mixed particles is, for example, 1:4. A detailed description of the RTS sequences is provided in WO 2006/040334, incorporated by reference herein. RTS may be in the form of mixed particles, RTS,S, where the ratio of RTS:S is, for example, 1:4. The protein designated RTS,S is a fusion protein consisting of the C-terminal half of the *P. falciparum* CS protein (17 of the central 41 NANP-repeats plus most of the C-terminal portion) expressed as a fusion protein with the Hepatitis B surface antigen.

The proteinaceous antigen comprising CS protein or immunogenic part thereof used as a priming vaccine hereof is adjuvanted, meaning that the priming composition comprises at least one adjuvant. Suitable adjuvants for use in the invention include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatized polysaccharides, polyphosphazenes, or montanide liposomes.

The adjuvant composition may be selected to induce a preferential Th1 response. Moreover, other responses, including other humoral responses, may also be induced.

Certain vaccine adjuvants are particularly suited to the stimulation of either Th1 or Th2-type cytokine responses. Traditionally, the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen-specific antibody responses. Thus, a Th1-type adjuvant is one that stimulates isolated T-cell populations to produce high levels of Th1-type cytokines when re-stimulated with antigen in vitro, and induces antigen-specific immunoglobulin responses associated with Th1-type isotype. For example, Th1-type immunostimulants that may be formulated to produce adjuvants suitable for use in the present invention may include Monophosphoryl lipid A, in particular, 3-de-O-acylated monophosphoryl lipid A (3D-MPL). 3D-MPL is a well-known adjuvant manufactured by Ribi Immunochem, Montana. Chemically, it is often supplied as a mixture of 3-de-O- acylated monophosphoryl lipid A with either four, five, or six acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099, EP 0729473 B1, EP 0549074 B1). In one embodiment, 3D-MPL is in the form of a particulate formulation having a small particle size less than 0.2 µm in diameter, and its method of manufacture is disclosed in EP 0689454.

Saponins are another example of Th1 immunostimulants that may be used with the invention. Saponins are well-known adjuvants. For example, Quil A (derived from the bark of the South American tree Quillaja Saponaria Molina), and fractions thereof, are described in U.S. Pat. No. 5,057,540, and EP 0362279 B1. The hemolytic saponins QS21 and QS17 (HPLC purified fractions of Quil A) have been described as potent systemic adjuvants, and the method of their production is disclosed in U.S. Pat. No. 5,057,540 and EP 0362279 B1. Also described in these references is the use of QS7 (a non-hemolytic fraction of Quil-A), which acts as a potent adjuvant for systemic vaccines. Combinations of QS21 and polysorbate or cyclodextrin are also known (WO 99/10008). Particulate adjuvant systems comprising fractions of QuilA, such as QS21 and QS7, are described in WO 96/33739 and WO 96/11711.

Yet another example of an immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 96/02555, EP 0468520).

Such immunostimulants as described above may be formulated together with carriers, such as, for example, liposomes, oil in water emulsions, and or metallic salts, including aluminium salts (such as aluminium hydroxide). For example, 3D-MPL may be formulated with aluminium hydroxide (EP 0689454) or oil in water emulsions (WO 95/17210); QS21 may be advantageously formulated with cholesterol-containing liposomes (WO 96/33739), oil in water emulsions (WO 95/17210) or alum (WO 98/15287); CpG may be formulated with alum or with other cationic carriers.

Combinations of immunostimulants may also be used, such as a combination of a monophosphoryl lipid A and a saponin derivative (WO 94/00153; WO 95/17210; WO 96/33739; WO 98/56414; WO 98/05355; WO 99/12565; WO 99/11241) or a combination of QS21 and 3D-MPL as disclosed in WO 94/00153. Alternatively, a combination of CpG plus a saponin such as QS21 may also be used in the present invention. Thus, suitable adjuvant systems include, for example, a combination of monophosphoryl lipid A, such as 3D-MPL, together with an aluminium salt. Another embodiment combines a monophosphoryl lipid A and a saponin derivative, such as the combination of QS21 and 3D-MPL as disclosed in WO 94/00153, or a less reactogenic composition where the QS21 is quenched in cholesterol-containing liposomes (DQ) as disclosed in WO 96/33739. Yet another adjuvant formulation involving QS21, 3D-MPL, and tocopherol in an oil-in-water emulsion is described in WO 95/17210. In another embodiment, CpG oligonucleotides are used alone or together with an aluminium salt.

A suitable adjuvant for use in the present invention is a preferential Th1-stimulating adjuvant, for example, an adjuvant comprising a saponin such as QS21 or a monophosphoryl lipid A derivative such as 3D-MPL, or an adjuvant comprising both of these optionally together with cholesterol-containing liposomes, as is described, for example, in WO 96/33739.

An adenovirus is used as a boosting vaccine herein. Adenoviruses for use as vaccines are well known and can be manufactured according to methods well known to the skilled person. The adenoviruses used for the invention are recombinant human adenoviruses of serotype 26 (Ad26) and 35 (Ad35). The advantage of this selection of human adenoviruses as vaccine vectors is that humans are not regularly infected with these wild-type adenoviruses, so that neutralizing antibodies against these serotypes are less prevalent in the human population at large (WO 00/70071). Recombinant adenoviruses can be produced to very high titers using cells that are considered safe, and that can grow in suspension to very high volumes, using medium that does not contain any animal- or human-derived components. Also, it is known that recombinant adenoviruses can elicit a dramatic immune response against the protein encoded by the heterologous nucleic acid sequence in the adenoviral genome.

In the genome of the adenovirus, the nucleic acid encoding the transgene(s), here the CS antigen or an immunogenic part thereof, is operably linked to expression control sequences. This can, for instance, be done by placing the nucleic acid encoding the transgene under the control of a promoter. Further regulatory sequences may be added. A convenient and routine way of doing this is cloning the transgene into an expression cassette, available in many formats from several expression plasmids sold by commercial vendors, which expression cassette usually contains sequences capable of bringing about expression of the nucleic acid, such as enhancer(s), promoter, polyadenylation signal, and the like. Several promoters can be used for expression of the transgenes, and these may comprise viral, mammalian, synthetic promoters, and the like. Non-limiting examples of suitable promoters for obtaining expression in eukaryotic cells, are the CMV-promoter (U.S. Pat. No. 5,385,839), a mammalian EF1-alpha promoter, a mammalian ubiquitin C promoter, or a SV40 promoter. In certain embodiments, a promoter driving the expression of the transgenes is the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgenes.

The administration of the adenovirus hereof will result in expression of the CS antigen in cells of the subject to which the adenovirus is administered. This will result in an immune response to CS in the subject. Thus, the invention provides methods and uses hereof, wherein the nucleic acid encoding the CS antigen is expressed in the subject. In certain aspects, the invention provides methods and uses hereof, so that an immune response against the CS antigen is induced.

Preferably, the adenoviral vector is deficient in at least one essential gene function of the E1 region, e.g., the E1a region and/or the E1b region, of the adenoviral genome that is required for viral replication. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). As known to the skilled person, in case of deletions of essential regions from the adenovirus genome, the functions encoded by these regions have to be provided in trans, preferably by the producer cell, i.e., when parts or whole of E1, E2 and/or E4 regions are deleted from the adenovirus, these have to be present in the producer cell, for instance, integrated in the genome, or in the form of so-called helper adenovirus or helper plasmids.

In certain embodiments, the adenovirus hereof lacks at least a portion of the E1-region, e.g., E1A and/or E1B coding sequences, and further comprises heterologous nucleic acid encoding the CS antigen or an immunogenic part thereof.

The construction of adenoviral vectors is well understood in the art and involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989); Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

Adenoviral vectors, methods for construction thereof, and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology*, B. N. Fields et al., eds., 3d ed., Raven Press, Ltd., New York (1996), and other references mentioned herein.

In preferred embodiments, the adenovirus is replication deficient, e.g., because it contains a deletion in the E1 region of the genome. For the adenoviruses hereof, being derived from Ad26 or Ad35, it is preferred to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as, for example, 293 cells, PER.C6® cells, and the like (see, e.g., Havenga et al., 2006; WO 03/104467, incorporated in its entirety by reference herein). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is preferred to retain the 3' end of the E1B 55K open reading frame in the adenovirus, for instance, the 166 bp directly upstream of the pIX open reading frame or a fragment comprising this, such as a 243 bp fragment directly upstream of the pIX start codon, marked at the 5' end by a Bsu36I restriction site, since this increases the stability of the adenovirus because the promoter of the pIX gene is partly residing in this area (see, e.g., Havenga et al., 2006; WO 2004/001032, incorporated by reference herein).

In certain embodiments, the nucleic acid encoding CS protein or immunogenic part thereof in the recombinant adenovirus vectors of the boosting compositions encode CS protein or immunogenic part thereof having the same amino acid sequence as the CS protein or immunogenic part thereof as present in the priming composition.

The adenovirus used in the invention comprises nucleic acid encoding CS antigen of a malaria-causing parasite such as *P. falciparum*. Such adenoviruses and ways of making these have been described before in Havenga et al., 2006; Ophorst et al., 2007; WO 2004/055187, all incorporated in their entirety by reference herein. In certain embodiments, the nucleic acid encodes the entire open reading frame of the CS antigen. In other embodiments, the adenovirus comprises fragments of the coding sequence of the CS antigen, which fragment comprises antigenic parts or epitopes of the CS protein. Preferably, at least part of the GPI signal sequence of the CS protein has been deleted (see, e.g., Ophorst et al., 2007). Such constructs have been described in great detail in the examples of WO 2004/055187 (clone 02-659; see FIG. 2 therein). Briefly, these adenovectors comprise a heterologous gene encoding for the CS protein with an amino acid sequence that is similar to the CS protein of the NF54 strain, 3D7 clone, having, amongst others, an N-terminal signal sequence, 27 NANP repeats, a cluster of three NVDP repeats and one separate NVDP repeat, the universal epitope (Lockyer et al., 1989; Zevering et al., 1994; Nardin et al., 2001), and a deletion of the last 14 amino acids (at the C-terminus). The difference with the protein of RTS,S is that RTS,S lacks the N-terminal signal sequence, and a large portion of the repeat region, as well as most of the C-terminally located GPI anchor signal sequence, which is also absent in the adenoviral constructs. In certain embodiments, the adenovirus comprises nucleic acid encoding a CS protein as provided by amino acids 1-372 of SEQ ID NO: 6 of WO 2004/055187, incorporated in its entirety by reference herein. See, also, SEQ NO:1 herein. In certain embodiments, the nucleic acid sequence encoding the antigens has been codon optimized for expression in humans. In certain embodiments, the adenovirus comprises a nucleic acid sequence comprising nucleotides 13-1128 of SEQ ID NO: 4 of WO 2004/055187, incorporated in its entirety by reference herein. See, also, SEQ NO:2 herein. The recombinant adenovirus of serotype 35 comprising nucleic acid encoding the CS antigen or an immunogenic part thereof, is also referred to herein as Ad35.CS. The recombinant adenovirus of serotype 26 comprising nucleic acid encoding the CS antigen or an immunogenic part thereof, is also referred to herein as Ad26.CS.

The adenoviruses used in the invention were thus already known as vaccines against malaria, and the instant invention discloses their use particularly preferred novel prime boost regimens. The superior immune responses obtained with these regimens could not be foreseen, given the many different permutations possible. In particular, the prior art actually taught in a completely opposite direction, since it was previously reported that a vaccine regimen of priming with Ad35.CS and boosting with CS protein (RTS,S) gave superior immune responses compared to the reverse regimen wherein CS protein was used as a priming vaccine and Ad35.CS was used as a booster (WO 2006/040334; Stewart et al., 2007). Thus, the instant invention is based on the surprisingly superior immune responses observed using the regimens of the instant invention, wherein the priming vaccine is a CS protein vaccine and the booster vaccines are Ad35.CS and Ad26.CS. In addition, the regimens of the instant invention differ from the most preferred regimens described before, wherein Ad35.CS prime was followed by two boosters with the adjuvanted proteinaceous CS-derived antigen RTS,S (WO 2006/040334; Stewart et al., 2007), since the regimens of the instant invention require only one administration of the adjuvanted CS protein or immunogenic part thereof. Advantages of the instant invention, therefore, include a lower need for expensive adjuvanted CS proteinaceous antigen (RTS,S), while Ad35.CS and Ad26.CS can be manufactured in economically more advantageous manner than the adjuvanted proteinaceoous antigen, and moreover, a lower risk for (local) adverse reactions due to the adjuvanted proteinaceous antigen in view of less administrations thereof.

Adenoviruses can be prepared, harvested and purified in cell culture systems well known in the art and, for instance, WO 2010/060719 and European patent application no. 10153581 of Crucell Holland B.V. as filed on 15 Feb. 2010, both incorporated by reference herein, describe suitable methods for obtaining and purifying large amounts of recombinant adenoviruses such as those used in the present invention. Further methods for producing and purifying adenoviruses are disclosed in, for example, WO 98/22588, WO 00/32754, WO 04/020971, U.S. Pat. Nos. 5,837,520, 6,261,823, WO 2005/080556, and WO 2006/108707, all incorporated by reference herein.

For administering to humans, pharmaceutical compositions comprising the adenovirus and a pharmaceutically acceptable carrier or excipient may be utilized. In the present context, the term "pharmaceutically acceptable" means that the carrier or excipient, at the dosages and concentrations employed, will not cause unwanted or harmful effects in the subjects to which they are administered. Such pharmaceutically acceptable carriers and excipients are well known in the art (see *Remington's Pharmaceutical Sciences*, 18th edition, A. R. Gennaro, Ed., Mack Publishing Company [1990]; *Pharmaceutical Formulation Development of Peptides and Proteins*, S. Frokjaer and L. Hovgaard, Eds., Taylor & Francis [2000]; and *Handbook of Pharmaceutical Excipients*, 3rd edition, A. Kibbe, Ed., Pharmaceutical Press [2000]). The purified adenovirus preferably is formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g., pH 5.0 to 7.5. The adenovirus or immunogenic parts thereof typically are in a solution having a suitable pharmaceutically acceptable buffer, and the solution of adenovirus may also contain a salt. In certain embodiments, detergent is present. In certain embodiments, the vaccine may be formulated into an injectable preparation. These formulations contain effective amounts of the adenovirus, are either sterile liquid solutions, liquid suspensions or lyophilized versions and optionally contain stabilizers or excipients. The vaccine can also be aerosolized for intranasal administration (see, e.g., WO 2009/117134).

For instance, the adenovirus may be stored in the buffer that is also used for the Adenovirus World Standard (Hoganson et al., "Development of a stable adenoviral vector formulation," *Bioprocessing* March 2002, p. 43-48): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can, for instance, be found in European Patent No. 0853660, U.S. Pat. No. 6,225,289 and in international patent applications WO 99/41416, WO 99/12568, WO 00/29024, WO 01/66137, WO 03/049763, WO 03/078592, and WO 03/061708.

In certain embodiments, one or both of the adenovirus booster vaccines further comprises an adjuvant. Adjuvants are known in the art to further increase the immune response to an applied antigenic determinant, and pharmaceutical compositions comprising adenovirus and suitable adjuvants are, for instance, disclosed in WO 2007/110409, incorporated by reference herein.

In other embodiments, the adenovirus vaccines used in the invention do not comprise further adjuvants.

In the methods or uses hereof, the dose of the adenovirus provided to a patient during one administration can be varied as is known to the skilled practitioner, and is generally between $1\times10^7$ viral particles (vp) and $1\times10^{12}$ vp, preferably between $1\times10^8$ vp and $1\times10^{11}$ vp, for instance, between $3\times10^8$ and $5\times10^{10}$ vp, for instance, between $10^9$ and $3\times10^{10}$ vp.

Administration of the vaccine hereof can be performed using standard routes of administration. Non-limiting embodiments include parenteral administration, such as by injection, e.g., into the blood stream, intradermal, intramuscular, etc., or mucosal administration, e.g., intranasal, oral, and the like. In one embodiment, the vaccine is administered by intramuscular injection into the deltoid muscle. The skilled person knows the various possibilities to administer a vaccine hereof, in order to induce an immune response to the antigen(s) in the vaccine.

In certain embodiments, the priming vaccine hereof (i.e., the adjuvanted proteinaceous antigen comprising CS protein or immunogenic part thereof) is administered to a subject when the subject has an age of between about 0 weeks and about 5 months, e.g., at about 4, 5, 6, 7, 8, 9, 10, 11, or 12 weeks after birth. In other embodiments, the priming vaccine is administered when the subject has an age of between about 5 and 17 months. In yet further embodiments, the priming vaccine is administered when the subject has an age of between about 1 and 20 years, e.g., between about 1 and 5 years, preferably between about 1 and 2 years.

In certain embodiments, the first boosting vaccine (i.e., the composition comprising a recombinant adenovirus vector that comprises nucleic acid encoding CS protein or immunogenic part thereof) is administered within about 2 weeks to 4 months after administering the priming vaccine, e.g., about 3, 4, 5, 6, 7, 8, 9, or 10 weeks after the administration of the priming vaccine to the subject. In other embodiments, the first boosting vaccine is administered between about 4 and 24 months after administering the priming vaccine. In yet further embodiments, the first boosting vaccine is administered between about 2 and 20 years, e.g., between about 2 and 15 years, preferably between about 2 and 10 years, more preferably between about 2 and 5 years after the administration of the priming vaccine to the subject.

In certain embodiments, the second boosting vaccine (i.e., the composition comprising a recombinant adenovirus vector that comprises nucleic acid encoding CS protein or immunogenic part thereof, and being of the other serotype than the first recombinant adenovirus vector, i.e., Ad26 if the first booster was Ad35 and vice versa) is administered within about 2 weeks to 4 months after administering the first boosting vaccine, e.g., about 3, 4, 5, 6, 7, 8, 9, or weeks after the administration of the first boosting vaccine to the subject. In other embodiments, the second boosting vaccine is administered between about 4 and 24 months after administering the first boosting vaccine. In yet further embodiments, the second boosting vaccine is administered between about 2 and 20 years, e.g., between about 2 and 15 years, preferably between about 2 and 10 years, more preferably between about 2 and 5 years after the administration of the first boosting vaccine to the subject.

In a preferred regimen, the priming vaccine is administered to the subject when the subject has an age of about 6 weeks, the first boosting vaccine is administered about 1 month later (subject age about 10 weeks), and the second boosting vaccine is administered about another month later (subject age about 14 weeks). This regimen would be suitable for combination with the WHO Expanded Program on Immunization (EPI) schedule, which is an important logistical advantage since the vaccines hereof could be administered during some of the same visits of or to health workers as already recommended for the EPI schedule. The EPI schedule comprises: administration at birth of BCG (a live and attenuated strain of *Mycobacterium bovis*, which is currently the only available vaccine against tuberculosis) and sometimes OPV (oral polio vaccine); administration at an age of six weeks of OPV, DTP (diphtheria, tetanus, pertussis vaccine) and Hib (*Haemophilus influenzae* type B vaccine); administration at an age of 10 weeks of OPV, DTP and Hib; administration at an age of 14 weeks of OPV, DTP and Hib; and administration at an age of 9 to 12 months of measles virus vaccine.

The adenovirus vaccine is administered more than once, i.e., one time the Ad35.CS vector is administered hereof, and the other administration of adenovirus hereof is of the Ad26.CS vector. This can be done in either order, as it has been observed by the inventors that the immune responses against the CS protein encoded by these vectors were similar when these vectors were administered with Ad35.CS as prime and Ad26.CS as booster as with Ad26.CS as prime and Ad35.CS as booster (not shown), and it is anticipated that the earlier priming with CS protein hereof will not change this. It is important that the prime boost regimen hereof uses three different vaccine compositions for prime, first boost and second boost, respectively. In certain embodiments, the first boosting composition comprises Ad35.CS and the second boosting composition comprises Ad26.CS.

In certain equivalent embodiments, the adenovirus vectors hereof are administered to a subject to which the CS protein or immunogenic fragment thereof has already been administered to the subject previously. Hence, the invention also provides embodiments wherein the boosting adenovirus vaccines are administered to a subject to which a priming composition comprising CS protein or immunogenic part thereof from a malaria-causing parasite has already been administered. In a further equivalent embodiment, the invention provides administering the second booster vaccine hereof to subjects to which the priming and first boosting composition have already been administered.

It is also possible to administer the adenovirus vaccine more than twice, e.g., three times, four times, etc., so that the first boosting vaccination is followed by more than one further boosting vaccination. Also, the adjuvanted proteinaceous antigen comprising CS protein or immunogenic part thereof from a malaria-causing parasite may be administered more than once to the subject, and the second or further administration of the proteinaceous antigen in such embodiments could be performed either before the administration of the first adenovirus hereof, between the first and second administration of adenovirus vector hereof, or after the administration of the second adenovirus vector hereof. However, it is preferred to administer the adjuvanted proteinaceous antigen comprising CS protein or immunogenic part thereof from a malaria-causing parasite to the subject only once. It is also possible to combine the regimens hereof with further administration of nucleic acid encoding the CS protein or an immunogenic part thereof, the nucleic acid being part of a different vector, e.g., an adenovirus of a serotype different from Ad35 and Ad26 such as a chimpanzee adenovirus or a human Ad5, Ad11, Ad34, Ad48, Ad49, Ad50, etc., or a DNA vector, or an MVA vector, etc. In further embodiments, the regimens hereof may be combined with the administration of further different malaria antigens, either as protein or in the form of (vectors comprising) nucleic acids encoding such proteins; such different malaria antigens to which immune responses can be generated are known to the skilled person and include, for instance, LSA-1.

In a further aspect, disclosed is a method or use similar to the disclosure, but wherein a composition comprising Ad35.CS is used as a priming vaccine, followed by a composition comprising Ad26.CS as a first boosting vaccine and adjuvanted proteinaceous antigen comprising CS or an immunogenic part thereof as a second boosting vaccine (Ad35.CS/Ad26.CS/CS prot); yet, alternatively, the priming and first boosting composition according to this aspect are reversed (Ad26.CS/Ad35.CS/CS prot).

The driving force behind the development of the immune responses is cytokines, a number of identified protein messengers that serve to help the cells of the immune system and steer the eventual immune response to either a Th1 or Th2 response. Thus, high levels of Th1-type cytokines tend to favor the induction of cell mediated immune responses to the given antigen, while high levels of Th2-type cytokines tend to favor the induction of humoral immune responses to the antigen. The distinction of Th1 and Th2-type immune responses is not absolute. In reality, an individual will support an immune response that is described as being predominantly Th1 or predominantly Th2. Traditionally, Th1-type responses are associated with the production of the IFN-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumor necrosis factor-α (TNF-α).

It has been observed that the administration of the vaccine to subjects according to the regimens hereof, gives rise to CD8+ T-cell responses to CS antigens.

In certain aspects, therefore, methods and uses hereof are provided, wherein the administration of the recombinant adenovirus vector induces a CD8+ T-cell response in the patient against the antigen encoded by the adenovirus vector, meaning that the patient has CD8 lymphocytes releasing cytokines, such as, for example, IL-2, IFN-γ or TNF-α. In certain embodiments, the CD8+ T-cell responses are boosted after a second administration of recombinant adenovirus vector. In certain embodiments, the CD8+ T-cell responses may be polyfunctional, meaning that T lymphocytes secrete more than one cytokine. Such polyfunctional T lymphocytes may increase the efficiency of the treatments hereof.

Methods for measuring antigen-specific cellular immune responses such as CD8+ and CD4+ T-cell responses are well known and routine to the skilled person, and include, for instance, ELISPOT, intracellular cytokine staining (ICS), and multiplex cytokine assays (see, e.g., Havenga et al., 2006; Ophorst et al., 2007; Stewart et al., 2007; Lemckert et al., 2005; O'Connor, 2004; Rodriguez et al., 2008, 2009). Methods for measuring antigen-specific humoral responses (B-cell responses) are also well known and routine to the skilled person, and include measuring antibodies against the antigen, such as by invasion assays and other assays that measure binding of antibodies to parasite or inhibition of parasite functionality (invasion, mobility, etc.), indirect immunofluorescence assay (IFA), or preferably by ELISA (see, e.g., Ophorst et al., 2007; Stewart et al., 2007; Rodriguez et al., 2008, 2009).

The invention is further explained in the following examples. The examples do not limit the invention in any way. They merely serve to clarify the invention.

EXAMPLES

Example 1

Studies in Mice

Materials and Methods

Vector and Protein Construction, Production and Purification

E1/E3-deleted, replication-incompetent Ad26 and Ad35 vectors expressing the same *P. falciparum* CS gene were generated in E1-complementing PER.C6® cells and purified using CsCl gradients as previously described (e.g., Havenga et al., 2006; WO 2004/055187). Viral particles (vp) were quantified by high-performance liquid chromatography (HPLC). The *P. falciparum* CS gene is a synthetic, mammalian-codon optimized insert encoding a CS protein based on the EMBL protein sequence CAH04007, and truncated for the last 14 amino acids at the C-terminus. The N-terminus of this CS protein is a consensus assembled by alignment of various sequences present in the GenBank, while the repeat region and the C-terminus are based on the sequence of the 3D7 *P. falciparum* clone. The CS repeat region consisted of 27 NANP repeats, a cluster of three NVDP and one separate NVDP. CS protein of identical sequence as in the adenovectors has been produced in *Hansenula polymorpha* RB11 clone by ARTES Biotechnology GmbH (Germany) A C-terminal His-tag sequence was introduced into the construct to facilitate Ni-column purification of the CS protein from the culture supernatant.

Characterization of the Yeast-Produced CS Protein

The yeast-produced CS protein was analyzed by CS-specific Western blot and InstantBlue staining, which demonstrated the identity and purity of the CS protein (more than 80% pure) (FIG. 1, Panel A). For the Western blot, rabbit polyclonal antibody against *P. falciparum* CS (MRA-24, MR4/ATCC) was used in combination with goat-anti-rabbit IgG conjugated to horseradish peroxide (HRP, Biorad) and enhanced chemiluminescence (ECL+, GE healthcare) to detect CS expression. The InstantBlue staining was performed according to protocol provided by the manufacturer (Expedeon).

A dose of the yeast-produced CS protein for prime-boost immunogenicity studies was selected using immunization of BALB/c mice (n=five per group) with increasing dosages of CS protein (5 µg, 10 µg or 25 µg), formulated with the Montanide ISA 720 (Seppic, France) at a 30:70 volume-based ratio, at three-week intervals. The CS-specific humoral responses were assessed using ELISA, which demonstrated that the yeast-produced CS protein induces maximal CS-specific antibody responses already at the lowest tested dose (5 µg) and after two immunizations (FIG. 1, Panel B). The induced IgG response consisted predominantly of IgG1 antibodies, indicating the Th2-type response (FIG. 1, Panel C). Analysis of the CS-specific cellular immunity using ELISPOT revealed poor induction of IFNγ+ T-cells for all doses (data not shown).

Animals and Vaccinations Regimens

Our study sought to evaluate whether vaccination with Ad35.CS and Ad26.CS can enhance the CS-specific immune response induced by a protein-based vaccine (e.g., RTS,S), as potential vaccination strategy for malaria. For these studies, we have used a yeast-produced full-length CS protein vaccine. Six- to eight-week-old female BALB/c mice were purchased from Harlan (Zeist, The Netherlands) and kept at the institutional animal facility under specific pathogen-free conditions during the experiment.

To evaluate the immunogenicity of the heterologous CS protein/Ad prime-boost regimens, BALB/c mice (n=eight per group) were primed at week 0 with 5 µg adjuvanted CS protein and boosted at week 4 with $10^9$ vp Ad35.CS. The optimal immunization doses of Ad.CS for immunization were selected from earlier dose response experiments (data not shown). Another group of mice (n=eight) received a homologous prime-boost regimen of 5 µg adjuvanted CS protein. As negative control group, BALB/c mice (n=six) were injected at week 0 with adjuvant montanide ISA720 and at week 4 with $10^9$ vp Ad35.Empty (adenovector without insert; indicated as sham immunization group).

To evaluate the three-component heterologous prime-boost, BALB/C mice (n=eight) were immunized at week 0 with 5 µg adjuvanted CS protein, boosted at week 4 with $10^9$ vp Ad35.CS and at week 8 with $10^{10}$ vp Ad26.CS. Comparator groups of BALB/C mice (n=eight per group) started immunization at week 4 with 5 µg adjuvanted CS protein and were boosted after four weeks (at week 8) with either $10^9$ vp Ad35.CS or 5 µg adjuvanted CS protein. As a negative control group, mice (n=three) received the adjuvant montanide ISA720 at week 0, $10^9$ vp rAd35.Empty at week 4 and $10^{10}$ vp rAd26.Empty at week 8.

CS-Specific T-Cell Assays

CS-specific cellular immune responses in vaccinated mice were assessed using interferon-γ (IFN-γ) ELISPOT assay, intracellular cytokine staining in combination with surface staining of CD4 and CD8 markers (ICS), as described previously elsewhere (Barouch et al., 2004; Rodriguez et al., 2008), and cytometric bead array (CBA) assay.

For the stimulation of splenocytes in the ELISPOT and ICS, a peptide pool consisting of eleven amino acids overlapping 15-mer peptides spanning the whole sequence of the *P. falciparum* CS protein was used. The pool contained a highly immunodominant CD8+ T-cell epitope (NYDNAGTNL (SEQ ID NO:3); H-2K$^d$), which is responsible for the main part of measured responses in the ELISPOT and the CD8+ responses in the ICS. This was confirmed with an experiment wherein the splenocytes were stimulated with the 9-mer peptides, which generated virtually identical responses as the peptide pool (data not shown). For the ELISPOT, 96-well multiscreen plates (Millipore, Bedford, Mass.) were coated overnight with 100 µl/well of 10 µg/ml anti-mouse IFN-γ (BD Phanningen, San Diego, Calif.) in endotoxin-free Dulbecco's PBS (D-PBS). The plates were then washed three times with D-PBS containing 0.05% TWEEN®-20 (D-PBS/TWEEN®), blocked for 2 hours with D-PBS containing 5% FBS at 37° C., and rinsed with RPMI 1640 containing 10% FBS. Splenocytes from individual mice were stimulated with the CS peptide pool for 18 hours at 37° C. Following incubation, the plates were washed six times with D-PBS/TWEEN® and once with distilled water. The plates were then incubated with 2 µg/ml biotinylated anti-mouse IFN-γ (BD Pharmingen, San Diego, Calif.) for 2 hours at room temperature, washed six times with D-PBS/TWEEN®, and incubated for 2 hours with a 1:500 dilution of streptavidin-alkaline phosphatase (Southern Biotechnology Associates, Birmingham, Ala.). Following six washes with D-PBS/TWEEN® and one with PBS, the plates were developed with nitro blue tetrazolium/5-bromo-4-chloro-3-indolyl-phosphate chromogen (Pierce, Rockford, Ill.), reaction was stopped with tap water, air dried, and read using an ELISPOT reader (Aelvis GmbH). Spot-forming units (SFU) per $10^6$ cells were calculated. In the case of the ICS, splenocytes from individual animals were stimulated with the CS peptide pool or cultured with medium alone. All cultures contained monensin (GolgiStop; BD Biosciences) as well as 1 µg/ml anti-CD49d (BD Biosciences).

The cultured cells were stained with monoclonal antibodies specific for cell surface molecules (CD4 and CD8). After fixing with Cytofix/Cytoperm solution (BD Biosciences), cells were permeabilized and stained with antibodies specific for mouse IFNγ. Approximately 200,000 to 1,000,000 events were collected per sample. The background level of cytokine staining was typically lower than 0.01% for CD4+ T cells and lower than 0.05% for CD8+ T cells.

The T-helper response induced by the different vaccination regimens was evaluated using Cytometric bead array (CBA) assay. Splenocytes from individual mice were stimulated with 5 μg/ml yeast-produced CS protein. After 48 hours of incubation at 37° C., supernatants were harvested and analyzed for the presence of the Th1 (IFNγ, TNFα, IL-2), Th2 (IL-4, IL-6, IL-10) and Th17 (IL-17) cytokines using the Mouse Th1/Th2/Th17 Cytokine Kit according to protocol provided by the manufacturer (BD Biosciences).

CS-Specific Antibody Assays

CS-specific antibody responses were assessed by enzyme-linked immunosorbent assay (ELISA) as previously described (Ophorst et al., 2007). Ninety-six-well microtiter plates (Maxisorp; Nunc) were coated overnight at 4° C. with 2 μg/ml of CS-specific $(NANP)_6C$ peptide in 0.05 M Carbonate buffer (pH 9.6). Plates were washed three times and blocked with PBS containing 1% BSA and 0.05% TWEEN®-20 for 1 hour at 37° C. After the plates were washed three times, 1:100-diluted individual serum samples were added to the wells and serially two-fold diluted in PBS containing 0.2% BSA and 0.05% TWEEN®-20. Plates were incubated for 2 hours at 37° C. Plates were washed three times and incubated with biotin-labeled anti-mouse or anti-rabbit immunoglobulin G (IgG) (Dako, Denmark), followed by horseradish peroxidase-conjugated streptavidin (Pharmingen San Diego, Calif.) for 30 minutes each at 37° C. For detection of the IgG subclasses, samples were incubated with horseradish peroxidase-labeled anti-mouse IgG1 or IgG2a antibodies (Southern Biotech, Birmingham, Ala.). Finally, the plates were washed and 100 μl of o-phenylenediamine dihydrochloride (OPD) substrate (Pierce, Rockford, Ill.) was added to each well. After 10 minutes, the reaction was stopped by adding 100 μl/well of 1 M $H_2SO_4$. The optical density was measured at 492 nm using a Bio-Tek reader (Bio-Tek Instruments, Winooski, Vt.). The ELISA units were calculated relative to the OD curve of the serially diluted standard serum, with one ELISA unit corresponding to the serum dilution at 50% of the maximum of the standard curve. The IgG2a/IgG1 ratio was determined using titer values of IgG1 and IgG2a antibodies, which are expressed as a reverse of serum dilution.

Statistical Analyses

Comparisons of geometric mean immune responses were performed by student t-test after logarithmic transformation to account for two test groups. Comparisons of geometric mean immune responses were performed by analyses of variance (ANOVA) with Tukey adjustments after logarithmic transformation to account for multiple comparisons. In all cases, p-values lower than 0.05 were considered significant.

Results

Immunogenicity of CS Protein Prime Followed by Ad35.CS Boost

Figure 2:
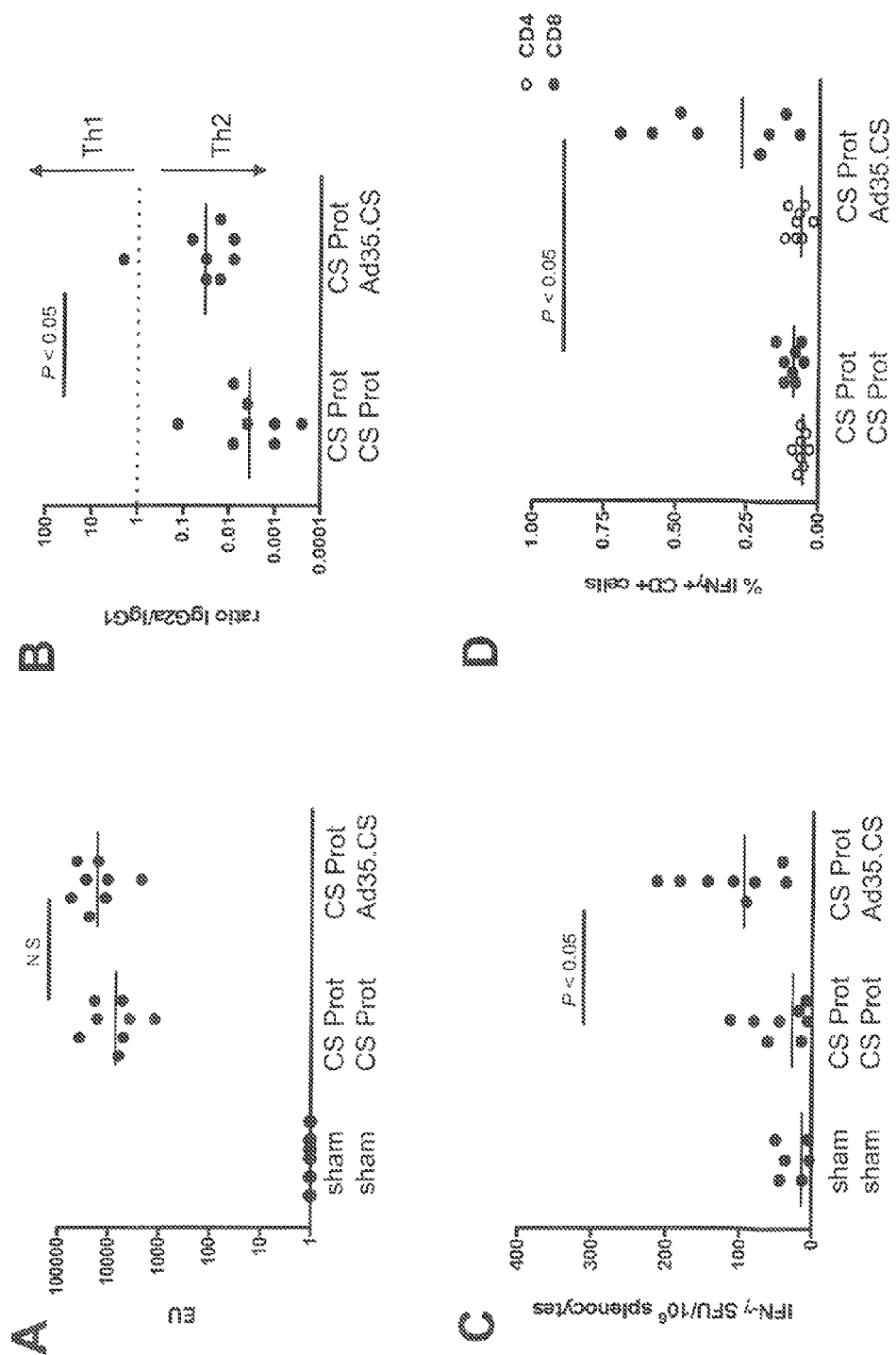
FIG. 2. Immunogenicity in mice of heterologous prime-boost regimen comprised of the yeast-produced CS protein and Ad35.CS. BALB/c mice (n=eight per group) were immunized as indicated in the graphs. A negative control group received the adjuvant and Ad35.Empty vector (sham). Two weeks after the boost immunization, CS-specific humoral immune responses were assessed by (A) CS-specific IgG responses using ELISA and (B) IgG2a/IgG1 ratios upon measurement of CS-specific IgG2a and IgG1 responses. CS-specific CD8+ T-cell immune responses were assessed by (C) IFNγ ELISPOT and (D) IFNγ ICS. Bars represent geometric means of (A) ELISA units (EU), (B) IgG2a/IgG1 ratios, (C) spot-forming units (SFU), or (D) percentage of IFNγ+ CD4+ or IFNγ+ CD8+ positive cells. The background level of cytokine staining was typically lower than 0.01% for the CD4+ T cells and lower than 0.05% for the CD8+ T cells.

CS-specific humoral response induced in BALB/c mice with a CS protein prime and Ad35.CS boost at two weeks post-immunization were assessed by ELISA assay (FIG. 2, Panels A and B) while the cellular immune responses were measured using IFNγ ELISPOT (FIG. 2, Panel C) and ICS (FIG. 2, Panel D). The homologous prime-boost regimen with the CS protein elicited a very potent CS-specific IgG response. The levels of the antibody response elicited by the heterologous CS protein/Ad35.CS regimen were comparable to that seen for the homologous CS protein prime-boost regimen (P>0.05 comparing CS-specific IgG levels with ANOVA). Beside the total CS-specific IgG levels, we determined the IgG2a/IgG1 ratio to obtain indications of the type of T-helper responses induced by the different prime-boost regimens (FIG. 2, Panel B). The homologous CS protein prime-boost regimen elicited primarily IgG1 antibody responses indicating a more Th2-type immune response while replacing the protein boost with Ad35.CS boost resulted in a more pronounced induction of IgG2a antibodies indicating shift toward a Th1-type response (P<0.05 comparing IgG2a/IgG1 ratios with ANOVA).

Evaluation of the CS-specific T-cell responses using ELISPOT (FIG. 2, Panel C) and ICS (FIG. 2, Panel D) assays showed that the homologous CS protein regimen evoked a poor but measurable CS-specific T-cell response. The inclusion of Ad35.CS as a boost to the CS protein prime resulted in significantly increased levels of CS-specific IFNγ-producing CD8+ T-cells (P<0.05 comparing CS-specific $CD8^+$ T-cell levels with ANOVA). This correlated to the more Th1-type response for the CS protein/Ad35.CS regimens as determined by CS-specific IgG2a/IgG1 ratio. It should be noted that IFNγ+CD4+ response might have been underestimated using the stimulation with the 15-mer peptides. Stimulation of splenocytes with the CS-protein in the current study did show higher CD4+ responses; however, the background in the assay was unacceptably high (not shown).

Immunogenicity of a Three-Component Heterologous Prime-Boost Regimen

Figure 3:
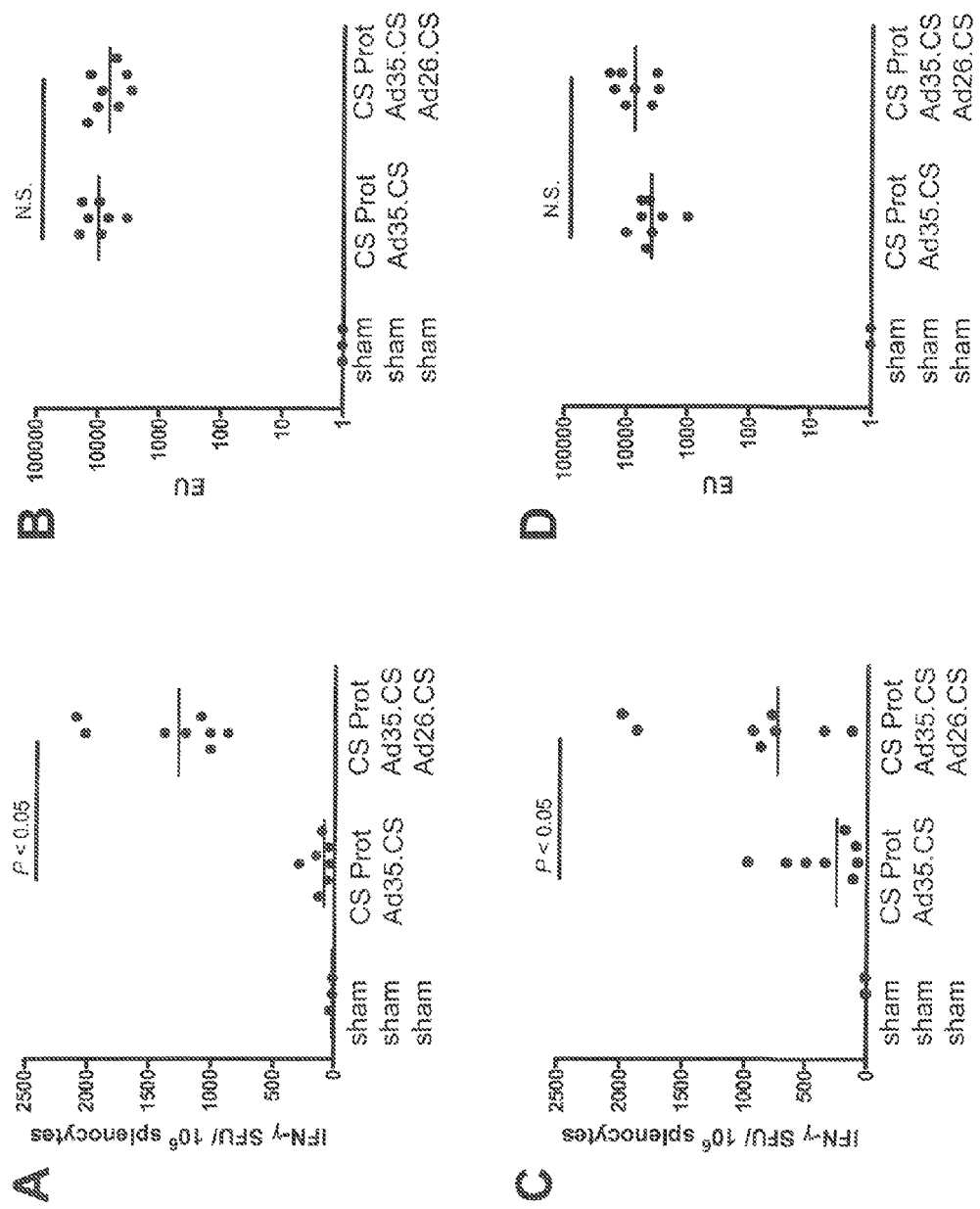
FIG. 3. Immunogenicity in mice of a three-component heterologous prime-boost regimen. BALB/c mice (n=eight per group) were immunized as indicated in the graphs. A negative control group received the adjuvant and Ad.Empty vectors (sham). Two weeks (A) and eight weeks (C) after the final boost immunization, CS-specific IFNγ+ CD8+ T-cell responses were assessed using ELISPOT. Two weeks (B) and eight weeks (D) after the final boost immunization, CS-specific humoral immune responses were assessed by IgG ELISA. Bars represent geometric means of (A, C) spot-forming units (SFU) or (B, D) ELISA units (EU).

The combination of the yeast-produced CS protein with the Ad35.CS in a heterologous prime-boost regimen results in the induction of high levels of IFNγ+ CD8+ T cells, maintained high levels of CS-specific IgG response and the antibody response was shifted toward the Th1 type. We next investigated whether a prime-boost regimen comprised of the three components, CS protein, Ad35.CS and Ad26.CS, might result in an even more robust and sustained Th1 immune response. Our earlier experiments demonstrated that the Ad35.CS/Ad26.CS combination induces significantly higher immune responses than the Ad35.CS/Ad35.CS combination (data not shown) and, therefore, the homologous adenovector combination Ad35.CS/Ad35.CS was not included as a booster vaccine in the current study. A group of mice received a prime with adjuvanted CS protein and a boost with Ad35.CS followed by a second boost with Ad26.CS (three-component heterologous prime-boost). A comparator group of mice received a prime with adjuvanted CS protein followed by an Ad35.CS boost. At two weeks post the final boost immunization, mice receiving the three-component heterologous prime-boost regimen showed significantly higher levels of CS-specific IFNγ-producing CD8+ T-cells compared to the mice receiving the CS protein prime and Ad35.CS boost regimen (FIG. 3, Panel A, P>0.05 comparing CS-specific IFNγ-producing CD8+ T-cell levels with ANOVA). At eight weeks post the final boost immunization, the IFNγ+ CD8+ T-cell response induced by the three-component prime-boost regimen was still significantly higher compared to the CS protein/Ad35.CS regimen (FIG. 3, Panel B; P>0.05 comparing CS-specific IFNγ-producing CD8+ T-cell levels with ANOVA). Importantly, at both time points, the levels of CS-specific IgG responses induced by the three-component prime-boost regimen were comparable to that seen for the CS protein/Ad35.CS regimen (FIG. 3, Panels B and D; P>0.05 comparing CS-specific IgG levels with ANOVA). The IgG2a/IgG1 ratio of CS-specific antibodies induced with the CS protein/Ad35.CS/Ad26.CS vaccine regimen was comparable to the ratio induced with the CS protein/Ad35.CS immunization (data not shown).

Cytokine Profile Induced by the Different Vaccination Regimens

Figure 4:
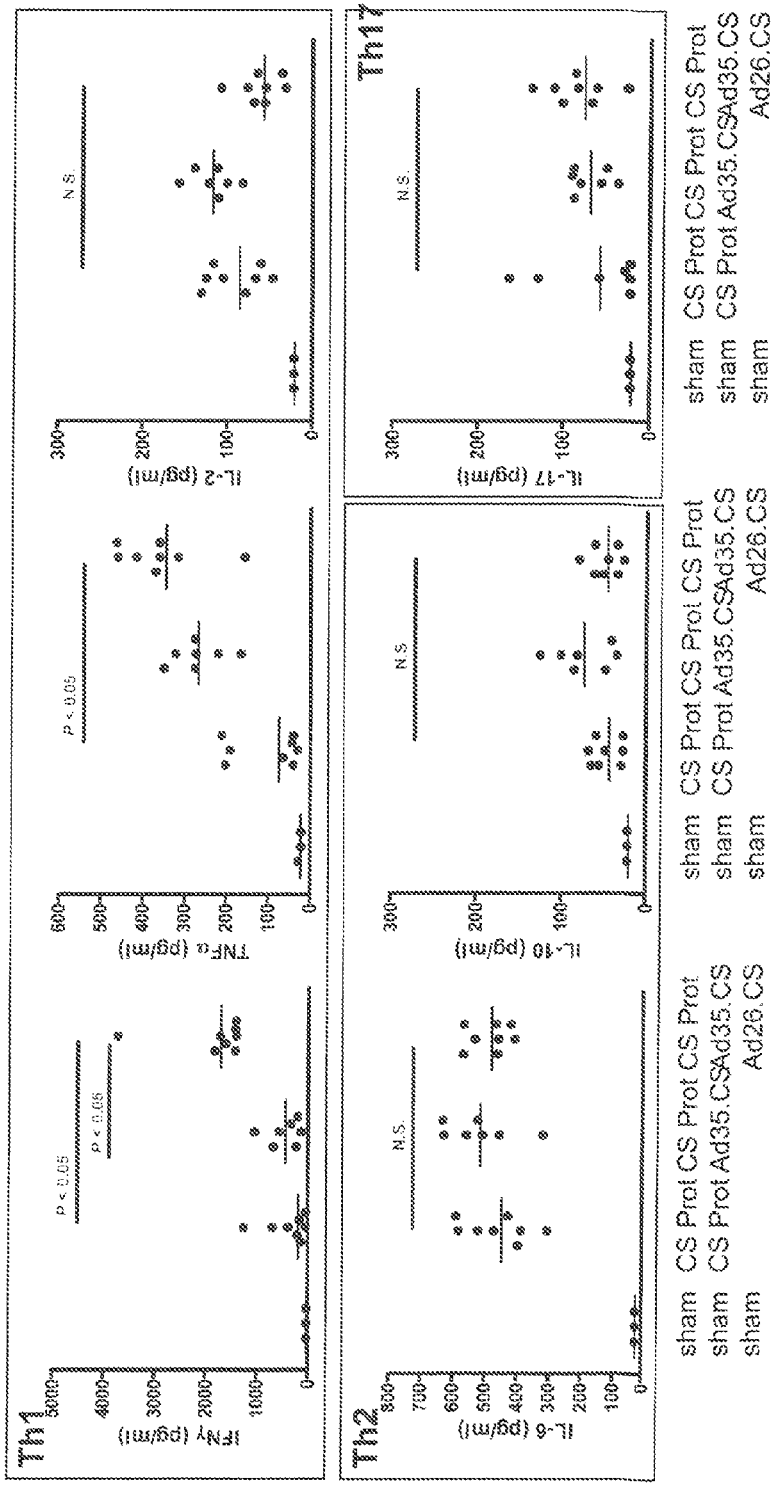
FIG. 4. Cytokine profile induced by the different vaccination regimens in mice. BALB/c mice (n=eight per group) were immunized as indicated in the graphs. A negative control group received the adjuvant and Ad.Empty vectors (sham). Two weeks after the final boost immunization, cytokine expression was assessed by CBA assay upon 48 hours in vitro stimulation of splenocytes with the CS protein. Bars represent geometric means of pg/ml IFNγ, TNFα, IL-2, IL-6, IL-10 or IL-17 cytokine levels. Measurable levels of IL-4 were not detected in any of the immunized mice.

The total number of CS-specific CD4+ T cells expressing two or more immune markers, being Th1 cytokines IFNγ, TNFα, IL2, and activation marker CD40L, induced upon immunization with RTS,S, has been associated with protection from malaria infection in the human challenge model (Kester et al., 2009). We investigated cytokine profile breadth induced in CS-specific T cells with three-component malaria vaccine, CS protein/Ad35.CS/Ad26.CS, and compared it to the cytokine profiles induced with CS-protein/CS protein or CS protein/Ad35.CS regimen. Two weeks after the final boost immunization, expression levels of the Th1 (IFNγ, TNFα, IL-2), Th2 (IL-4, IL-6, IL-10) and Th17 (IL-17) cytokines were determined using the cytometric bead array (CBA) assay upon 48 hours in vitro stimulation of splenocytes with the CS protein. The CBA assay with protein stimulation provides a blueprint of the type of T helper cells that have been induced with the vaccination regimen. All vaccination regimens, except for the sham, induced the tested cytokines, with an exception of IL-4, which was not detected (data not shown) (FIG. 4). The CS protein/Ad35.CS/Ad26.CS regimen induced significantly higher levels of IFNγ and TNFα compared to either the CS protein or the CS protein/Ad35.CS regimen (FIG. 4; $P<0.05$ comparing cytokine levels with ANOVA). The levels of other cytokines (IL-2, IL-6, IL-10 and IL17) were comparable for all immunization regimens (FIG. 4; $P>0.05$ comparing cytokine levels with ANOVA).

Summarizing, these data confirm that a prime-boost regimen comprised of the three components, CS protein, Ad35.CS and Ad26.CS, results in a robust and broad Th1-type immune response.

Discussion

Immunizations with a CS protein vaccine elicit potent antibody responses, but poor cellular responses. In this study, we demonstrated that vaccination with the CS protein followed by Ad35.CS vector in a heterologous prime-boost regimen results in enhancement of IFNγ+ CD8+ T-cell responses. The boosting with Ad35.CS did not hamper the level of CS-specific humoral response induced with the protein vaccination, but shifted the Ig isotypes toward a Th1 type of response. In addition, we established that a heterologous prime-boost regimen comprising a CS protein prime followed by boosts with Ad35.CS and Ad26.CS elicits strong CS-specific Th1-type responses, with a durable enhancement of the IFNγ+ CD8+ T-cells and potent antibody responses.

Adenoviral vectors are known to induce high levels of antigen-specific IFN-γ+ CD8+ T cells. The combination of adenovectors with other vaccine types has proven highly efficient in eliciting strong and sustainable T-cell immunity as well as humoral responses. Indeed, within the current study, we show that the priming with an adjuvanted yeast-produced CS protein followed by the Ad35.CS boost results in the induction of higher CS-specific IFN-γ+ CD8+ T-cell responses compared to exclusively protein-based vaccine regimen. Importantly, while the overall CS-specific IgG levels were not affected compared to the responses induced with an entirely CS protein vaccination regimen, the CS protein/Ad35.CS regimen elicited a more Th1-type response. These results corroborated earlier findings in which prime-boost regimens comprised of Ad35 vaccine vectors expressing CS or LSA-1, and RTS,S or a LSA-1 protein vaccine resulted in potent Th1 type T-cell responses and high level humoral responses (Rodriguez et al., 2008; Stewart et al., 2007).

Previously, we reported on the heterologous prime-boost regimen utilizing the Ad35.CS and Ad5.CS vaccine vectors that elicited high levels of CS-specific IFN-γ producing T cells in both mice and non-human primates (Rodriguez et al., 2009). These results demonstrated the potential of adenovector-based heterologous prime-boost regimens to induce the type of immunity required to combat malaria. Given the wide diversity of adenoviruses in nature, many different serotypes are potentially available. In our study, the inclusion of the Ad26.CS boost to the CS protein/Ad35.CS prime-boost regimen elicited an overall higher and more sustainable CS-specific IFNγ+ CD8+ immune response as compared to the homologous or the two-component heterologous prime-boost regimens.

The recent association of Th1 cytokine-expressing CD4+ T cells, induced with RTS,S vaccine, with protection against malaria infection in the human challenge model, has reinforced the view that induction of a broad immune response of Th1 type is required for development of efficient malaria vaccines (Kester et al., 2009). Induction of balanced pro-inflammatory and regulatory immune responses is also a key factor determining the outcome of malaria infection. Failure to develop an effective pro-inflammatory response might result in unrestricted parasite replication, whereas failure to control this response can lead to the development of severe immunopathology. Boosting of the CS protein vaccine with the Ad35.CS/Ad26.CS combination strongly enhanced the levels of Th1 cytokines IFNγ and TNFα, while the levels of Th1 cytokine IL-2, Th2 cytokines IL-6 and IL-10 and Th17 cytokine IL-17 were comparable to the levels induced with the CS protein vaccine alone. This result indicated the capacity of the three-component regimen to stimulate an overall balanced cytokine response, with a strong shift toward the Th1 responses as compared to the homologous CS protein regimen inducing primarily a Th2-biased response. While the role for Th1-type response in protection against malaria has been well documented, to our knowledge, there are no reports concerning the role of Th17 cells in malaria infection. However, there is mounting evidence that IL-17 might be relevant for protection against parasitic infections and other pathogens. In the current study, albeit no significant difference was observed in the mean level of the IL-17 cytokines between different groups, the adenovector-containing regimens induced more uniform IL-17 responses as compared to the protein immunization.

The limited and short-lived protection induced with the CS protein vaccine can be strongly improved as demonstrated in the current study, by administering the Ad35.CS/Ad26.CS combination as a booster vaccine (in second year of life or even at school age) following an early-in-life protein CS vaccine, to induce long-lasting protection for which the Th1-type response and immune memory is required.

A further study in non-human primates evaluates the prime-boost regimen combining the CS protein vaccine, Ad35.CS and Ad26.CS. The study comprises three experimental groups of five animals each. One group receives a prime with the CS protein followed by a first boost with Ad35.CS and a second boost with Ad26.CS. Another group receives a prime with Ad35.CS followed by a first boost with Ad26.CS and a second boost with the CS protein. A third group receives a prime with Ad35.CS followed by a first boost with Ad35.CS and a second boost with Ad26.CS. The vaccination schedule involves intramuscular administration of the vaccines at zero, four, and eight weeks. Methods for measuring antigen-specific cellular immune responses such as CD8+ and CD4+ T-cell responses comprises ELISPOT, ICS, and multiplex cytokine assays. Methods for measuring antigen-specific humoral responses include ELISA.

Example 2

Study in Non-Human Primates

The tolerability and immunogenicity of the three-component prime-boost was evaluated in non-human primates. For this purpose, rhesus macaques (15 animals in total) were selected from an available animal pool based on following criteria: (i) physical exam demonstrating good health, (ii) no prior exposure to malaria or malaria antigens (no background in CS-specific ELISA and ELISPOT assays), and (iii) no detectable neutralizing antibodies against Ad35 or Ad26 in serum. Selected animals were stratified over three experimental treatment groups, five animals each, on the basis of body weight, age and gender. Eventually, all three treatment groups contained two male and three female individuals each. Animals were socially housed throughout the study.

Animals were vaccinated at weeks 0, 4 and 8 by intramuscular injection under sedation with adjuvant-formulated or rAd-vectored circumsporozoite (CS) protein from *P. falciparum* (Pf). CS protein was formulated in Matrix M adjuvant from Isconova (Uppsala). Vaccine injections were given contralaterally in the left and right upper arm (triceps) and the upper leg (quadriceps), respectively. The immunization schedules including dose are listed in Table 1.

TABLE 1

Immunization schedules non-human primate study

| Group | N | Abbrev. Treatm. | Vaccine - 1st, 2nd & 3rd - | Dosage |
|---|---|---|---|---|
| T1 | 5 | Ad35/Ad35/Ad26 | rAd35.CS | $3 \times 10^{11}$ vp |
| | | | rAd35.CS | $3 \times 10^{11}$ vp |
| | | | rAd26.CS | $3 \times 10^{11}$ vp |
| T2 | 5 | Ad35/Ad26/CS | rAd35.CS | $3 \times 10^{11}$ vp |
| | | | rAd26.CS | $3 \times 10^{11}$ vp |
| | | | CS in MatrixM | 50 µg |
| T3 | 5 | CS/Ad35/Ad26 | CS in MatrixM | 50 µg |
| | | | rAd35.CS | $3 \times 10^{11}$ vp |
| | | | rAd26.CS | $3 \times 10^{11}$ vp |

Immune responses were assayed for 24 weeks upon primary vaccination. Briefly, blood samples were drawn, by venipuncture under sedation, for collection of PBMC and serum samples and cryo storage. Humoral immunity was measured by CS-specific ELISA using recombinant CS protein and a CS-specific peptide (NANP)$_6$C (rCS, CS.p). Cellular immunity was measured by IFNγ-specific ELISPOT (SPOT), upon stimulation of frozen PBMCs with recombinant CS protein and CS-specific pool of peptides. Finally, the anti-vector responses were evaluated using neutralization assays specific for Ad35 and Ad26.

Results

Local Adverse Effects

Animals were observed as a daily routine of animal care and, at sedation time points, the injection sites were specifically inspected. Around the vaccination time points, no abnormalities at the site of injection were observed, neither upon primary, secondary or tertiary vaccination by intramuscular injection of either of the adjuvanted CS protein or the Ad35.CS or Ad26.CS vaccine candidates.

CS-Specific Response

Figure 5:
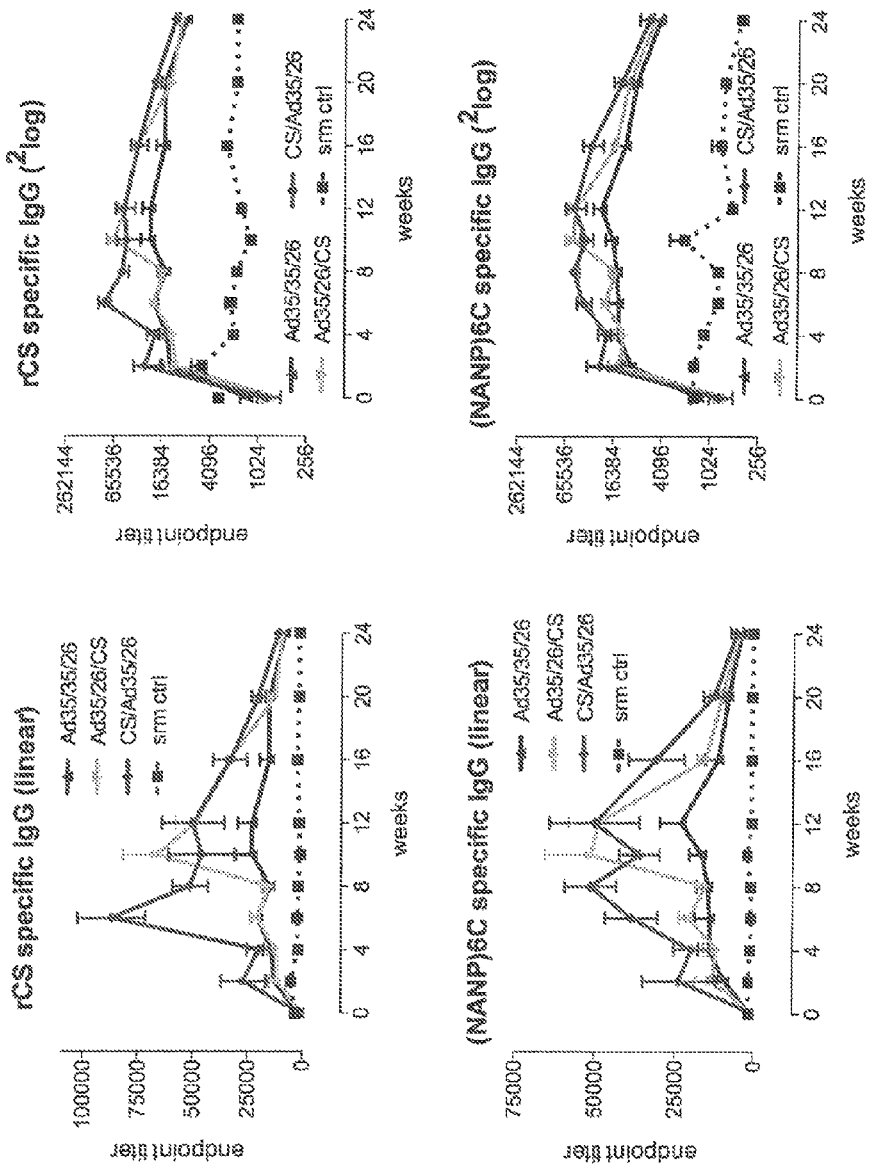
FIG. 5. CS-specific humoral immunity induced by the three-component regimen in non-human primates. The CS-specific humoral response was measured by ELISA using CS protein (top panels) and CS (NANP)$_6$C peptide (bottom panels) for coating. Data is depicted in a linear as well as a $^2$log scale on the left and the right, respectively.

CS-specific IgG responses were measured by ELISA using serial dilutions of sera to determine the samples' endpoint titers, which were defined as the lowest titer at which signals were exceeding 2× saline control values. As a positive control, a titration range of a positive serum pool from naturally exposed individuals from an endemic region was used (control serum). Endpoint titers in time and per treatment group are depicted in FIG. 5 (data are depicted in a linear as well as a $^2$log scale on the left and the right, respectively). Upon primary vaccination, the Ad35.CS and the CS protein induced similar CS-specific IgG levels. Upon secondary vaccination, animals primed with the CS-protein and boosted with Ad35.CS showed the highest levels of CS-specific antibody responses, as compared to animals receiving an Ad35.CS prime and boosted with either Ad35.CS or the Ad26.CS. Upon tertiary vaccination the three-component vaccination regimens (CS protein/Ad35.CS/Ad26.CS and Ad35.CS/Ad26.CS/CS protein) showed comparable CS-specific antibody levels, which were somewhat higher than the levels shown by the Ad35.CS/Ad35.CS/Ad26.CS. However, toward week 20 of the study, the CS-specifc antibody response induced by all vaccination regimens were comparable, suggesting no major impact on the longevity of specific humoral immunity by either of these vaccination regimes.

Figure 6:
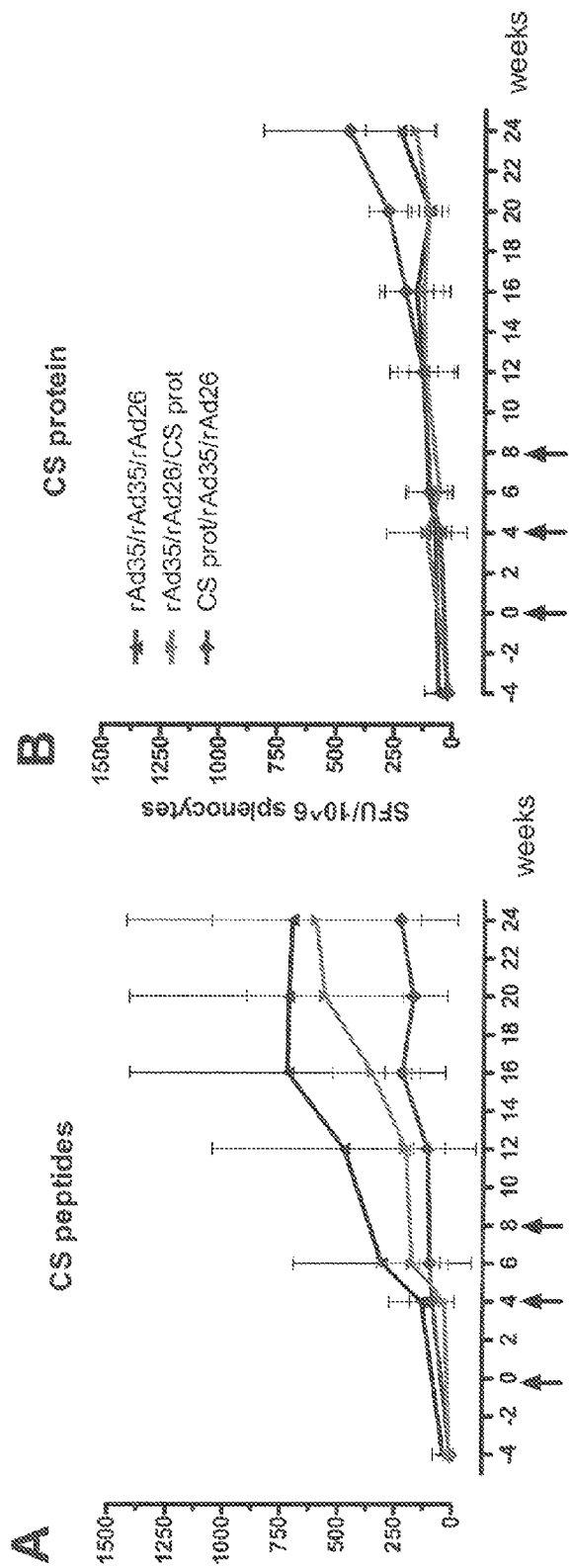
FIG. 6. CS-specific cell-mediated immunity induced by the three-component regimen in non-human primates. IFNγ responses were measured by ELISPOT using frozen PBMCs from several time points throughout the study. PBMC were defrosted and 5×10$^5$ cells were stimulated overnight in triplicate with 15 μg/ml CS protein (A) and 1 μg/ml CS peptide pool (B). Results are depicted as mean spot-forming units (SFU)±SD.

The CS-specific cellular responses induced by the vaccination regimens were measured using IFN-γ ELISPOT and are depicted in FIG. 6. All vaccination regimens showed high CS-specific IFN-γ cellular responses upon stimulation with CS peptide pool and CS protein. The numbers of IFN-γ spot-forming units were higher upon stimulation with the CS peptide pool stimulation as compared to the CS protein stimulation, suggesting the activation of different cell types. Interestingly, upon stimulation with CS peptide pool, the Ad35.CS/Ad35.CS/Ad26.CS regimen showed the highest IFN-γ response, whereas, upon stimulation with CS protein, the CS protein/Ad35.CS/Ad26.CS regimen showed the best results.

Adenovector-Specific Response

Figure 7:
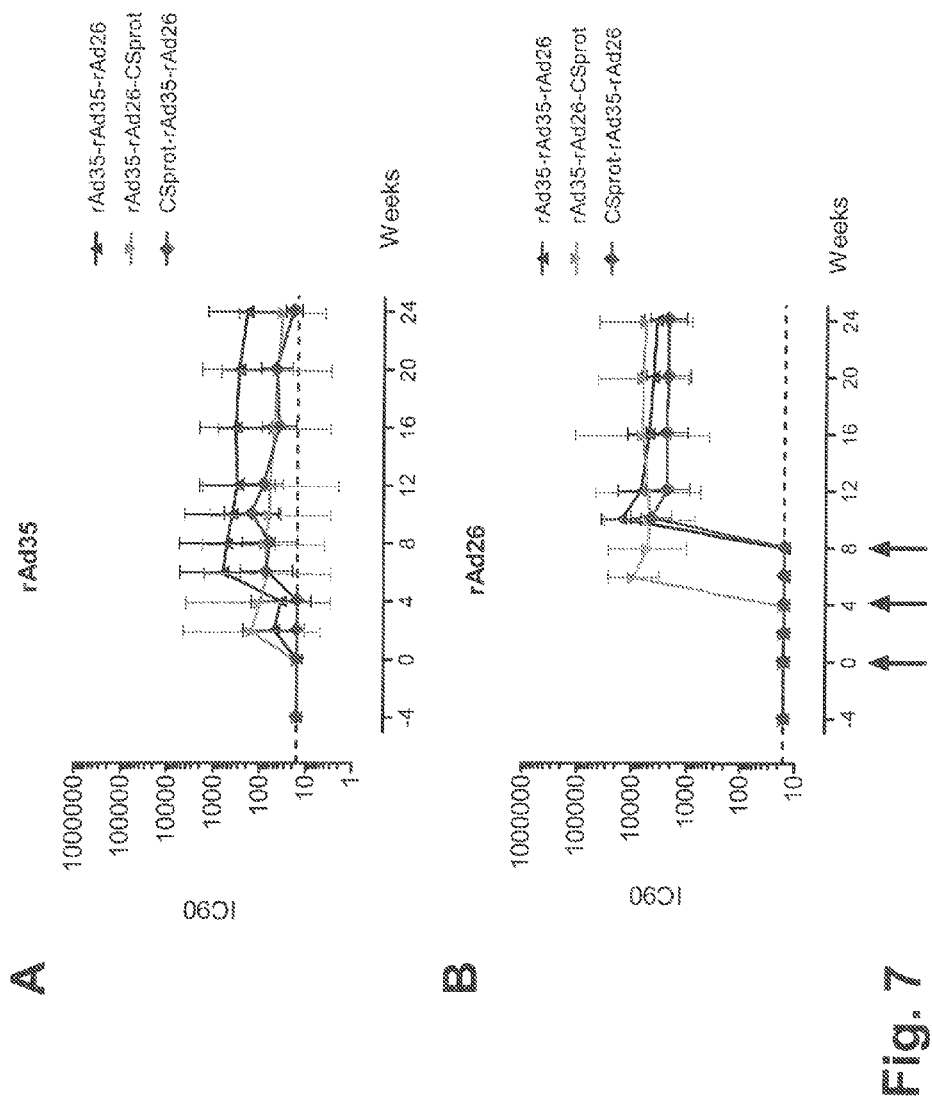
FIG. 7. Neutralizing antibodies against rAd35 (A) and Ad26 (B) upon immunization of non-human primates. Black arrows indicate immunization time points. Data is presented as geometric means +/−95% confidence interval.

The evaluation of the vector-specific responses was performed using neutralization assays specific for Ad35 and Ad26. The levels of neutralizing antibodies against Ad35 and Ad26 vectors are depicted in FIG. 7. Data showed that all animals immunized with the adenovectors elicited Ad35- and Ad26-neutralizing antibodies. Low titers of Ad35 neutralizing antibodies are induced upon a single vaccination with Ad35.CS, indicating the feasibility of a second vaccination with the same vector. Upon the second Ad35.CS vaccination, the levels of neutralizing antibodies increased significantly. The levels of neutralizing antibodies against Ad26 were higher than the levels seen for Ad35.

In conclusion, the non-human primate study confirmed our earlier data in mice showing that a three-component heterologous prime-boost including adjuvanted CS protein/Ad35.CS/Ad26.CS, is a highly efficient regimen inducing antibody and T-cell responses that are required for protection against malaria.

REFERENCES

Abbink P., A. A. C. Lemckert, B. A. Ewald, D. M. Lynch, et al. 2007. Comparative seroprevalence and immunogenicity of six rare serotype-recombinant adenovirus vaccine vectors from subgroups B and D. *J. Virol.* 81:4654-4663.

Barouch D. H., M. G. Pau, J. H. Custers, W. Koudstaal, et al. 2004. Immunogenicity of recombinant adenovirus serotype 35 vaccine in the presence of pre-existing anti-Ad5 immunity. *J. Immunol.* 172:6290-7.

Bejon P., J. Lusingu, A. Olotu, A. Leach, et al. 2008. Efficacy of RTS,S/AS01 E vaccine against malaria in children 5 to 17 months of age. *N Engl. J. Med.* 359:2521-32.

Cayabyab M. J., B. Korioth-Schmitz, Y. Sun, A. Carville, et al. 2009. Recombinant *Mycobacterium bovis* BCG Prime-Recombinant Adenovirus Boost Vaccination in Rhesus Monkeys Elicits Robust Polyfunctional Simian Immunodeficiency Virus-Specific T-Cell Responses. *J. Virol.* 83:5505-5513.

Havenga M., R. Vogels, D. Zuijdgeest, K. Radosevic, et al. 2006. Novel replication-incompetent adenoviral B-group vectors: high vector stability and yield in PER.C6® cells. *J. Gen. Virol.* 87:2135-2143.

Kester K. E., J. F. Cummings, O. Ofori-Anyinam, C. F. Ockenhouse, et al. 2009. Randomized, double-blind, phase 2a trial of falciparum malaria vaccines RTS,S/AS01B and RTS,S/AS02A in malaria-naive adults: safety, efficacy, and immunologic associates of protection. *J. Infect. Dis.* 200: 337-46.

Lemckert A. A., S. M. Sumida, L. Holterman, R. Vogels, et al. Immunogenicity of heterologous prime-boost regimens involving recombinant adenovirus serotype 11 (Ad11) and Ad35 vaccine vectors in the presence of anti-Ad5 immunity. *J. Virol.* 2005 August; 79(15):9694-701.

O'Connor K. A., A. Holguin, M. K. Hansen, S. F. Maier, L. R. Watkins. A method for measuring cytokines from small samples. *Brain, Behaviour and Immunity*, 2004, 18(3): 274-280.

Ophorst O. J., K. Radosevic, M. J. Havenga, M. G. Pau, et al. 2006. Immunogenicity and protection of a recombinant human adenovirus serotype 35-based malaria vaccine against *Plasmodium yoelii* in mice. *Infect. Immun.* 74:313-20.

Ophorst O. J., K. Radosevic, K. Ouwehand, W. van Beem, et al. 2007. Expression and immunogenicity of the *Plasmodium falciparum* circumsporozoite protein: the role of GPI signal sequence. *Vaccine* 25:1426-36.

Radošević K., C. W. Wieland, A. Rodriguez, G. J. Weverling, et al. 2007. Protective immune responses to a recombinant adenovirus type 35 Tuberculosis vaccine in two mouse strains: CD4 and CD8 T-cell epitope mapping and role of gamma interferon. *Infect. Immunity* 75:4105-4115.

Rodrigues E. G., F. Zavala, D. Eichinger, J. M. Wilson, and M. Tsuji. 1997. Single immunizing dose of recombinant adenovirus efficiently induces CD8+ T cell-mediated protective immunity against malaria. *J. Immunol.* 158:1268-74.

Rodriguez A., J. Goudsmit, A. Companjen, R. Mintardjo, et al. 2008. Impact of recombinant adenovirus serotype 35 priming versus boosting of a *Plasmodium falciparum* protein: characterization of T- and B-cell responses to liver-stage antigen 1. *Infect. Immun.* 76:1709-18.

Rodriguez A., R. Mintardjo, D. Tax, G. Gillissen, et al. 2009. Evaluation of a prime-boost vaccine schedule with distinct adenovirus vectors against malaria in rhesus monkeys. *Vaccine* 27:6226-33.

Stewart V. A., S. M. McGrath, P. M. Dubois, M. G. Pau, et al. 2007. Priming with an adenovirus 35-circumsporozoite protein (CS) vaccine followed by RTS,S/AS01B boosting significantly improves immunogenicity to *Plasmodium falciparum* CS compared to that with either malaria vaccine alone. *Infect. Immun.* 75:2283-90.

The invention claimed is:

1. A method for inducing an immune response in a subject against an antigen from a malaria-causing parasite, the method comprising:
   (i) administering to a subject a priming composition comprising adjuvanted proteinaceous antigen comprising circumsporozoite (CS) protein from a malaria-causing parasite;
   (ii) administering to the subject a first boosting composition comprising a recombinant adenovirus vector that comprises nucleic acid encoding CS protein from a malaria-causing parasite; and
   (iii) administering to the subject a second boosting composition comprising a recombinant adenovirus vector that comprises nucleic acid encoding CS protein from a malaria-causing parasite,
   wherein either the first boosting composition comprises a recombinant adenovirus vector of serotype 35 (Ad35) and the second boosting composition comprises a recombinant adenovirus of Ad26, or
   wherein the first boosting composition comprises a recombinant adenovirus vector of Ad26 and the second boosting composition comprises a recombinant adenovirus of Ad35.

2. A method for inducing an immune response in a subject against an antigen from a malaria-causing parasite, the method comprising:
   administering to a subject to which a priming composition comprising adjuvanted proteinaceous antigen comprising CS protein from a malaria-causing parasite has been administered:
   (a) a first boosting composition comprising a recombinant adenovirus vector that comprises nucleic acid encoding CS protein; and
   (b) a second boosting composition comprising a recombinant adenovirus vector that comprises nucleic acid encoding CS protein,
   wherein either the first boosting composition comprises a recombinant adenovirus vector of serotype 35 (Ad35) and the second boosting composition comprises a recombinant adenovirus of Ad26, or
   wherein the first boosting composition comprises a recombinant adenovirus vector of Ad26 and the second boosting composition comprises a recombinant adenovirus of Ad35.

3. A method for inducing an immune response in a subject against an antigen from a malaria-causing parasite, the method comprising:
   administering to a subject to which a priming composition comprising adjuvanted proteinaceous antigen comprising CS protein from a malaria-causing parasite, and a first boosting composition comprising a recombinant adenovirus vector that comprises nucleic acid encoding CS protein have been administered:
   a second boosting composition comprising a recombinant adenovirus vector that comprises nucleic acid encoding CS protein,
   wherein either the first boosting composition comprises a recombinant adenovirus vector of serotype 35 (Ad35) and the second boosting composition comprises a recombinant adenovirus of Ad26, or
   wherein the first boosting composition comprises a recombinant adenovirus vector of Ad26 and the second boosting composition comprises a recombinant adenovirus of Ad35.

4. The method according to claim 1, wherein the first boosting composition comprises a recombinant adenovirus vector of Ad35 and the second boosting composition comprises a recombinant adenovirus of Ad26.

5. The method according to claim 1, wherein the malaria-causing parasite is *Plasmodium falciparum*.

6. The method according to claim 1, wherein the adjuvanted proteinaceous antigen comprising circumsporozoite (CS) protein from a malaria-causing parasite in the priming composition comprises RTS,S.

7. The method according to claim 1, wherein the immune response comprises a CS specific CD8+ T-cell response.

8. The method according to claim 1, wherein the immune response comprises inducing CS specific IFNγ+ CD8+ and TNFα+ CD8+ T-cells.

9. The method according to claim 1, wherein the immune response comprises a Th1 type T-cell response.

10. The method according to claim 1, wherein inducing the immune response comprises shifting the CS specific immune response from a Th2 type towards a balanced Th1 and Th2 type or a predominant Th1 type of response.

11. The method according to claim 1, wherein the immune response comprises a CS specific B-cell response.

12. The method according to claim 1, wherein the priming composition is administered or has been administered to the subject where the subject had or has an age of about 6 weeks, and wherein the first boosting composition is administered or has been administered to the subject about 4 weeks after administration of the priming composition and the second boosting composition is administered to the subject about 4 weeks after administration of the first priming composition.

13. The method according to claim 2, wherein the first boosting composition comprises a recombinant adenovirus vector of Ad35 and the second boosting composition comprises a recombinant adenovirus of Ad26.

14. The method according to claim 2, wherein the malaria-causing parasite is *Plasmodium falciparum*.

15. The method according to claim 2, wherein the adjuvanted proteinaceous antigen comprising circumsporozoite (CS) protein or immunogenic part thereof from a malaria-causing parasite in the priming composition comprises RTS,S.

16. The method according to claim 2, wherein the immune response comprises a CS specific CD8+ T-cell response.

17. The method according to claim 3, wherein the first boosting composition comprises a recombinant adenovirus vector of Ad35 and the second boosting composition comprises a recombinant adenovirus of Ad26.

18. The method according to claim 3, wherein the malaria-causing parasite is *Plasmodium falciparum*.

19. The method according to claim 3, wherein the adjuvanted proteinaceous antigen comprising circumsporozoite (CS) protein or immunogenic part thereof from a malaria-causing parasite in the priming composition comprises RTS,S.

20. The method according to claim 3, wherein the immune response comprises a CS specific CD8+ T-cell response.

* * * * *

SEQUENCE LISTING

```
<160> NUMBER OF SEQ ID NOS: 4

<210> SEQ ID NO 1
<211> LENGTH: 372
<212> TYPE: PRT
<213> ORGANISM: Plasmodium falciparum
<220> FEATURE:
<221> NAME/KEY: SIGNAL
<222> LOCATION: (1)..(30)
<223> OTHER INFORMATION: Signal sequence region
<220> FEATURE:
<221> NAME/KEY: REPEAT
<222> LOCATION: (124)..(259)
<223> OTHER INFORMATION: Region of 4 NVDP and in total 30 NAVP repeats
<220> FEATURE:
<221> NAME/KEY: LIPID
<222> LOCATION: (359)..(372)
<223> OTHER INFORMATION: GPI-ANCHOR

<400> SEQUENCE: 1

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95
```

```
Gly Asn Asn Glu Asp Asn Glu Lys Leu Arg Lys Pro Lys His Lys Lys
            100                 105                 110

Leu Lys Gln Pro Ala Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Val Asp Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Lys Asn Asn Gln Gly Asn Gly Gln Gly His
            260                 265                 270

Asn Met Pro Asn Asp Pro Asn Arg Asn Val Asp Glu Asn Ala Asn Ala
        275                 280                 285

Asn Ser Ala Val Lys Asn Asn Asn Glu Glu Pro Ser Asp Lys His
    290                 295                 300

Ile Lys Glu Tyr Leu Asn Lys Ile Gln Asn Ser Leu Ser Thr Glu Trp
305                 310                 315                 320

Ser Pro Cys Ser Val Thr Cys Gly Asn Gly Ile Gln Val Arg Ile Lys
                325                 330                 335

Pro Gly Ser Ala Asn Lys Pro Lys Asp Glu Leu Asp Tyr Ala Asn Asp
            340                 345                 350

Ile Glu Lys Lys Ile Cys Lys Met Glu Lys Cys Ser Ser Val Phe Asn
        355                 360                 365

Val Val Asn Ser
    370

<210> SEQ ID NO 2
<211> LENGTH: 1154
<212> TYPE: DNA
<213> ORGANISM: Artificial
<220> FEATURE:
<223> OTHER INFORMATION: Codon-optimised circumsporozoite gene of
      Plasmodium falciparum strain 3D7
<220> FEATURE:
<221> NAME/KEY: CDS
<222> LOCATION: (13)..(1128)
<223> OTHER INFORMATION: Nucleic acid sequence encoding translated
      protein
<220> FEATURE:
<221> NAME/KEY: sig_peptide
<222> LOCATION: (13)..(102)
<223> OTHER INFORMATION: Nucleic acid sequence encoding signal sequence
      of translated protein

<400> SEQUENCE: 2
aagcttgcca cc atg atg agg aaa ctg gcc atc ctg agc gtg agc agc ttc     51
              Met Met Arg Lys Leu Ala Ile Leu Ser Val Ser Ser Phe
                1               5                   10
```

```
ctg ttc gtg gag gcc ctg ttt cag gag tac cag tgc tac ggc agc agc      99
Leu Phe Val Glu Ala Leu Phe Gln Glu Tyr Gln Cys Tyr Gly Ser Ser
    15              20                  25 agc aac acc cgg gtg ctg aac gag ctg aac tac gac aac gcc ggc acc     147
Ser Asn Thr Arg Val Leu Asn Glu Leu Asn Tyr Asp Asn Ala Gly Thr
30              35                  40                  45 aac ctg tac aac gag ctg gag atg aac tac tac ggc aag cag gag aac     195
Asn Leu Tyr Asn Glu Leu Glu Met Asn Tyr Tyr Gly Lys Gln Glu Asn
                50                  55                  60 tgg tac agc ctg aag aag aac agc cgg tct ctg ggc gag aac gac gac     243
Trp Tyr Ser Leu Lys Lys Asn Ser Arg Ser Leu Gly Glu Asn Asp Asp
            65                  70                  75 ggc aac aac aac aac ggc gac aac ggc cgg gag ggc aag gac gag gac     291
Gly Asn Asn Asn Asn Gly Asp Asn Gly Arg Glu Gly Lys Asp Glu Asp
        80                  85                  90 aag cgg gac ggc aac aac gag gac aac gag aag ctg cgg aag ccc aag     339
Lys Arg Asp Gly Asn Asn Glu Asp Asn Glu Lys Leu Arg Lys Pro Lys
    95                  100                 105 cac aag aaa ctt aag cag ccc gcc gac ggc aac ccc gac ccc aac gcc     387
His Lys Lys Leu Lys Gln Pro Ala Asp Gly Asn Pro Asp Pro Asn Ala
110             115                 120                 125 aac ccc aac gtg gac ccc aac gcc aat cct aat gtc gac ccc aat gcc     435
Asn Pro Asn Val Asp Pro Asn Ala Asn Pro Asn Val Asp Pro Asn Ala
                130                 135                 140 aat ccg aac gtt gat ccc aat gcg aat cct aac gct aac ccc aat gcc     483
Asn Pro Asn Val Asp Pro Asn Ala Asn Pro Asn Ala Asn Pro Asn Ala
            145                 150                 155 aac cca aat gcc aat cca aat gca aat ccc aac gcc aat cca aac gca     531
Asn Pro Asn Ala Asn Pro Asn Ala Asn Pro Asn Ala Asn Pro Asn Ala
        160                 165                 170 aac cct aat gct aat cca aac gct aat cct aat gcc aat ccc aat gct     579
Asn Pro Asn Ala Asn Pro Asn Ala Asn Pro Asn Ala Asn Pro Asn Ala
    175                 180                 185 aac cca aac gtc gat cct aac gca aat ccg aac gct aac ccc aac gca     627
Asn Pro Asn Val Asp Pro Asn Ala Asn Pro Asn Ala Asn Pro Asn Ala
190                 195                 200                 205 aat ccc aac gct aac ccg aac gca aac cct aac gcc aat ccg aat gcc     675
Asn Pro Asn Ala Asn Pro Asn Ala Asn Pro Asn Ala Asn Pro Asn Ala
                210                 215                 220 aac cca aac gcc aac ccg aac gct aat ccg aat gct aac ccg aat gct     723
Asn Pro Asn Ala Asn Pro Asn Ala Asn Pro Asn Ala Asn Pro Asn Ala
            225                 230                 235 aat cct aac gca aac cca aat gca aac ccc aat gca aac ccg aac gcc     771
Asn Pro Asn Ala Asn Pro Asn Ala Asn Pro Asn Ala Asn Pro Asn Ala
        240                 245                 250 aat ccc aac gcc aat cct aat gcc aac aag aac aat cag ggc aac ggc     819
Asn Pro Asn Ala Asn Pro Asn Ala Asn Lys Asn Asn Gln Gly Asn Gly
    255                 260                 265 cag ggc cac aac atg ccc aac gac ccc aac cgg aac gtg gac gag aac     867
Gln Gly His Asn Met Pro Asn Asp Pro Asn Arg Asn Val Asp Glu Asn
270                 275                 280                 285 gcc aac gcc aac agc gcc gtg aag aac aac aac aac gag gag ccc agc     915
Ala Asn Ala Asn Ser Ala Val Lys Asn Asn Asn Asn Glu Glu Pro Ser
                290                 295                 300 gac aag cac atc aag gag tac ctg aac aag atc cag aac agc ctg agc     963
Asp Lys His Ile Lys Glu Tyr Leu Asn Lys Ile Gln Asn Ser Leu Ser
            305                 310                 315 acc gag tgg agc ccc tgc agc gtg acc tgc ggc aac ggc att cag gtg    1011
Thr Glu Trp Ser Pro Cys Ser Val Thr Cys Gly Asn Gly Ile Gln Val
        320                 325                 330
```

```
cgg atc aag ccc ggc agc gcc aac aag ccc aag gac gag ctg gac tac    1059
Arg Ile Lys Pro Gly Ser Ala Asn Lys Pro Lys Asp Glu Leu Asp Tyr
        335                 340                 345 gcc aat gac atc gag aag aag atc tgc aag atg gag aag tgc agc agc    1107
Ala Asn Asp Ile Glu Lys Lys Ile Cys Lys Met Glu Lys Cys Ser Ser
350                 355                 360                 365 gtg ttc aac gtg gtg aac tcc tgataaagat ctgctgataa ggatcc           1154
Val Phe Asn Val Val Asn Ser
                370

<210> SEQ ID NO 3
<211> LENGTH: 372
<212> TYPE: PRT
<213> ORGANISM: Artificial
<220> FEATURE:
<223> OTHER INFORMATION: Synthetic Construct

<400> SEQUENCE: 3

Met Met Arg Lys Leu Ala Ile Leu Ser Val Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Ala Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Val Asp Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Lys Asn Asn Gln Gly Asn Gly Gln Gly His
            260                 265                 270

Asn Met Pro Asn Asp Pro Asn Arg Asn Val Asp Glu Asn Ala Asn Ala
        275                 280                 285

Asn Ser Ala Val Lys Asn Asn Asn Glu Glu Pro Ser Asp Lys His
    290                 295                 300
```

```
Ile Lys Glu Tyr Leu Asn Lys Ile Gln Asn Ser Leu Ser Thr Glu Trp
305                 310                 315                 320

Ser Pro Cys Ser Val Thr Cys Gly Asn Gly Ile Gln Val Arg Ile Lys
                325                 330                 335

Pro Gly Ser Ala Asn Lys Pro Lys Asp Glu Leu Asp Tyr Ala Asn Asp
                340                 345                 350

Ile Glu Lys Lys Ile Cys Lys Met Glu Lys Cys Ser Ser Val Phe Asn
            355                 360                 365

Val Val Asn Ser
        370

<210> SEQ ID NO 4
<211> LENGTH: 9
<212> TYPE: PRT
<213> ORGANISM: Plasmodium falciparum

<400> SEQUENCE: 4

Asn Tyr Asp Asn Ala Gly Thr Asn Leu
1               5
```